(12) United States Patent
Muerhoff et al.

(10) Patent No.: US 11,340,230 B2
(45) Date of Patent: May 24, 2022

(54) SUBJECT ANTI-HCV ANTIBODY DETECTION ASSAYS EMPLOYING NS3 CAPTURE PEPTIDES

(71) Applicant: Abbott Laboratories, Abbott Park, IL (US)

(72) Inventors: Anthony S. Muerhoff, Kenosha, WI (US); John C. Prostko, Kenosha, WI (US); Christopher C. Marohnic, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 49 days.

(21) Appl. No.: 17/071,976

(22) Filed: Oct. 15, 2020

(65) Prior Publication Data

US 2021/0041442 A1 Feb. 11, 2021

Related U.S. Application Data

(63) Continuation of application No. 16/122,261, filed on Sep. 5, 2018, now Pat. No. 10,816,551, which is a continuation of application No. 14/925,778, filed on Oct. 28, 2015, now Pat. No. 10,088,483.

(60) Provisional application No. 62/072,266, filed on Oct. 29, 2014.

(51) Int. Cl.
*G01N 33/576* (2006.01)

(52) U.S. Cl.
CPC ... *G01N 33/5767* (2013.01); *G01N 2333/186* (2013.01); *G01N 2333/914* (2013.01); *G01N 2469/20* (2013.01)

(58) Field of Classification Search
None
See application file for complete search history.

(56) References Cited

U.S. PATENT DOCUMENTS

| | | |
|---|---|---|
| 5,006,309 A | 4/1991 | Khalil et al. |
| 5,063,081 A | 11/1991 | Cozzette et al. |
| 5,089,424 A | 2/1992 | Khalil et al. |
| 5,135,785 A | 8/1992 | Meucci et al. |
| 5,241,070 A | 8/1993 | Law |
| 5,242,828 A | 9/1993 | Bergstrom et al. |
| 5,294,404 A | 3/1994 | Grandone et al. |
| 5,352,803 A | 10/1994 | Mattingly |
| 5,359,093 A | 10/1994 | Adamczyk et al. |
| 5,468,646 A | 11/1995 | Mattingly et al. |
| 5,496,925 A | 3/1996 | Mattingly |
| 5,543,524 A | 8/1996 | Mattingly et al. |
| 5,573,904 A | 11/1996 | Mattingly |
| 5,593,896 A | 1/1997 | Adamczyk et al. |
| 5,783,699 A | 7/1998 | Mattingly et al. |
| 6,225,047 B1 | 3/2001 | Hutchens et al. |
| 6,329,209 B1 | 12/2001 | Wagner et al. |
| 6,727,092 B2 | 4/2004 | Shah et al. |
| 9,194,873 B2 | 11/2015 | Dawson |
| 9,194,878 B2 | 11/2015 | Oonuma et al. |
| 9,790,478 B2 | 10/2017 | Muerhoff et al. |
| 10,088,483 B2 | 10/2018 | Muerhoff et al. |
| 2003/0170881 A1 | 9/2003 | Davis et al. |
| 2004/0018577 A1 | 1/2004 | Campbell et al. |
| 2004/0152070 A1 | 8/2004 | Shah et al. |
| 2005/0014136 A1 | 1/2005 | Depla et al. |
| 2005/0054078 A1 | 3/2005 | Miller et al. |
| 2005/0095584 A1 | 5/2005 | Seidel et al. |
| 2006/0160164 A1 | 7/2006 | Miller et al. |
| 2008/0020401 A1 | 1/2008 | Grenier et al. |
| 2008/0113339 A1 | 5/2008 | Rodgers |
| 2008/0248493 A1 | 10/2008 | Mattingly |
| 2012/0009196 A1 | 1/2012 | Muerhoff et al. |
| 2014/0272931 A1 | 9/2014 | Ziemann et al. |
| 2014/0272932 A1 | 9/2014 | Muerhoff et al. |
| 2014/0272933 A1 | 9/2014 | Dawson et al. |
| 2017/0052184 A1 | 2/2017 | Shah |

FOREIGN PATENT DOCUMENTS

| | | |
|---|---|---|
| CN | 101477126 A | 7/2009 |
| CN | 103792354 A | 5/2014 |
| EP | 04741293 | 2/1992 |
| JP | H08127592 A | 5/1996 |
| JP | 2733138 B2 | 12/1997 |
| JP | 2002512370 A | 4/2002 |
| JP | 2006516741 A | 7/2006 |
| WO | WO 91/15771 | 10/1991 |
| WO | WO 99/51773 | 10/1999 |
| WO | WO 99/54735 | 10/1999 |
| WO | WO 00/56934 | 9/2000 |
| WO | WO 02/096941 | 12/2002 |
| WO | WO 2008/027942 A2 | 3/2008 |
| WO | WO 2008/070727 | 6/2008 |
| WO | WO 2016/069762 | 5/2016 |

OTHER PUBLICATIONS

U.S. Appl. No. 60/878,017, Holets-McCormack, filed Dec. 29, 2006.
Adamczyk et al., "Chemiluminescence quenching of pteroic acid-N-sulfonyl-acridinium-9-carboxamide conjugates by folate binding protein," Bioorg. Med. Chem. Lett. 4: 2313-2317 (2004).
Adamczyk et al., "Chemiluminescent acridinium-9-carboxamide boronic acid probes: Application to a homogeneous glycated hemoglobin assay," Bioorg. Med. Chem. Lett. 16: 1324-1328 (2006).

(Continued)

*Primary Examiner* — Agnieszka Boesen
(74) *Attorney, Agent, or Firm* — Casimir Jones S.C.; Lisa Mueller

(57) ABSTRACT

The present disclosure provides methods, kits, and compositions for detecting subject anti-HCV antibodies in a sample using NS3 capture peptides. In certain embodiments, at least two NS3 helicase (NS3h) capture peptides and at least two conjugate peptides (e.g., NS3h conjugate peptides) are employed together, which allows for a broad dynamic range of subject antibody detection in a one-step type assay. In other embodiments, methods are provided of detecting NS3-specific subject antibodies without the use of a reducing agent. In some embodiments, NS3-specific subject antibodies are detected with a 'double shot' of NS3 conjugate peptide (e.g., conjugate peptide added to a sample both before and after washing).

16 Claims, 9 Drawing Sheets

Specification includes a Sequence Listing.

(56) References Cited

OTHER PUBLICATIONS

Adamczyk et al., "Homogeneous chemiluminescent assays for free choline in human plasma and whole blood," Anal. Chim. Acta 579(1): 61-67 (2006).

Adamczyk et al., "Intrinsic factor-mediated modulation of cyanocobalamin-N-sulfonyl-acridinium-9-carboxamide chemiluminescence," Biorg. Med. Chem. Lett. 14: 3917-3921 (2004).

Adamczyk et al., "Linker-Mediated Modulation of the Chemiluminescent Signal from N10-(3Sulfopropyi)-N-sulfonylacridinium-9-carboxamide Tracers." Bioconjugate Chem. 11: 714-724 (2000).

Adamczyk et al., "Modulation of the Chemiluminescent Signal from N10-(3-Sulfopropyi)-N10-Sulfonylacridinium-9-carboxamides," Tetrahedron 55: 10899-10914 (1999).

Adamczyk et al., "Neopentyl 3-Triflyloxypropanesulfonate. A Reactive Sulfopropylation Reagent for the Preparation of Chemiluminescent Labels," J. Org. Chem. 63: 5636-5639 (1998).

Adamczyk et al., "Regiodependent Luminescence Quenching of Biotinylated N-Sulfonyl-acridinium-9-carboxamides by Avidin," Org. Lett. 5: 3779-3782 (2003).

Adamczyk et al., "Synthesis of a Chemiluminescent Acridinium Hydroxylamine (AHA) for the Direct Detection of Abasic Sites in DNA," Org. Lett. 1:779-781 (1999).

Bian et al.: "Significance of Monoclonal Antibodies against the Conserved Epitopes within Non-Structural Protein 3 Helicase of Hepatitis C Virus", Plos One, vol. 8, No. 7, Jul. 24, 2013 (Jul. 24, 2013), p. e70214.

Bird et al., "Single-Chain Antigen-Binding Proteins," Science 242: 423-426 (1988).

Haugland, Handbook of Fluorescent Probes and Research Chemicals (1996).

Huston et al., "Protein engineering of antibody binding sites: Recovery of specific activity in an anti-digoxin single-chain Fv analogue produced in *Escherichia coli*," PNAS USA 85: 5879-5883 (1988).

Invitation to Pay Additional Fees for Application No. PCT/US2015/057845 dated Feb. 18, 2016 (8 pages).

International Search Report and Written Opinion for Application No. PCT/US2015/057845 dated May 25, 2016 (19 pages).

Mattingly et al., In Luminescence Biotechnology: Instruments and Applications; Dyke, K. V. Ed.; CRC Press: Boca Raton, pp. 77-105 (2002).

Mattingly, "Chemiluminescent 10-Methyl-Acridinium-9-(N-Sulphonylcarboxamide) Salts. Synthesis and Kinetics of Light Emission," J. Biolumin. Chemilumin. 6: 107-114 (1991).

McCafferty et al., "Phage antibodies: filamentous phage displaying antibody variable domains," Nature 348: 552-554 (1990).

McCapra et al., "Chemiluminescence involving peroxide decompositions," Photochem. Photobiol. 4: 1111-21 (1965).

Morota, et al., "A new sensitive and automated chemiluminescent microparticle immunoassay for quantitative determination of hepatitis C virus core antigen," J. Virol. Meth., 2009, 157:8-14.

Polak and Van Noorden, Introduction to Immunocytochemistry, 2nd ed., Springer Verlag, N.Y. (1997).

Razavi et al., "Stable and versatile active acridinium esters I," Luminescence 15: 239-244 (2000).

Razavi et al., "Stable and versatile active acridinium esters II," Luminescence 15: 245-249 (2000).

Schatz et al. (1993) "Use of Peptide Libraries to Map the Substrate Specificity of a Peptide-Modifying Enzine: A 13 Residue Consensus Peptide Specifies Biotinylation in *Escherichia coli*," Biotechnology, 11: 1138-1143.

Shah et al., "Combination HCV core antigen and antibody assay on a fully automated chemiluminescence analyzer." Transfusion. Aug. 2003;43(8):1067-74.

Wallemacq et al., "Evaluation of the New AxSYM Cyclosporine Assay: Comparison with TDx Monoclonal Whole Blood and EMIT Cyclosporine Assays," Clin. Chem. 45:432-435 (1999).

Weiss et al., "In Vivo Biotinylated Recombinant Antibodies: Construction, Characterization, and Application of a Bifunctional Fab-BCCP Fusion Protein Produced in *Escherichia coli*," (1994) Protein Expression & Purif, 5(5):509-17.

Wells, High Throughput Bioanalytical Sample Preparation. Methods and Automation Strategies, Elsevier (2003).

Wu et al., "Double-antigen sandwich time-resolved immunofluorometric assay for the detection of anti-hepatitis C virus total antibodies with improved specificity and sensitivity", Journal of Medical Microbiology., vol. 57, No. 8, Aug. 1, 2008 (Aug. 1, 2008), pp. 947-953.

Yatscoff et al., "Abbott TDx Monoclonal Antibody Assay Evaluated for Measuring Cyclosporine in Whole Blood," Clin. Chem. 36: 1969-1973 (1990).

Japanese Search Report Application No. 2017-523343 dated Apr. 14, 2020, 3 pages.

NS3-D1 (amino acids 1192-1356)

FIG. 1A. NS3-D1 Amino Acid Sequence (SEQ ID NO:2)
MAVDFIPVENLETTMRSPVFTDNSSPPVVPQSFQVAHLHAPTGSGKSTKVPAAYAAQGYKVLVLNPSVAA
TLGFGAYMSKAHGIDPNIRTGVRTITTGSPITYSTYGKFLADGGCSGGAYDIIICDECHSTDATSILGIG
TVLDQAETAGARLVVLATATPPGSVTGSGSGHHHHHH

FIG. 1B. NS3-D1-Cbt Amino Acid Sequence (SEQ ID NO:3)
MAVDFIPVENLETTMRSPVFTDNSSPPVVPQSFQVAHLHAPTGSGKSTKVPAAYAAQGYKVLVLNPSVAA
TLGFGAYMSKAHGIDPNIRTGVRTITTGSPITYSTYGKFLADGGCSGGAYDIIICDECHSTDATSILGIG
TVLDQAETAGARLVVLATATPPGSVTGSGSGHHHHHHGGGLNDIFEAQKIEWHE

NS3-D1, DelN15 (amino acids 1205-1356)

FIG. 1C. NS3-D1, delN15-Cbt (v2e) Amino Acid Sequence (SEQ ID NO:1)
MRSPVFTDNSSPPVVPQSFQVAHLHAPTGSGKSTKVPAAYAAQGYKVLVLNPSVAATLGFGAYMSKAHGI
DPNIRTGVRTITTGSPITYSTYGKFLADGGCSGGAYDIIICDECHSTDATSILGIGTVLDQAETAGARLV
VLATATPPGSVTGGGLNDIFEAQKIEWHEGHHHHHH

FIG. 1D. NS3-D1, delN15-XC9 Amino Acid Sequence (SEQ ID NO:13)
MRSPVFTDNSSPPVVPQSFQVAHLHAPTGSGKSTKVPAAYAAQGYKVLVLNPSVAATLGFGAYMSKAHGI
DPNIRTGVRTITTGSPITYSTYGKFLADGGCSGGAYDIIICDECHSTDATSILGIGTVLDQAETAGARLV
VLATATPPGSVTNNNNNNNNNNDECHAADRGGCGHHHHHH

FIG. 1E. NS3-D1, delN15 Amino Acid Sequence (SEQ ID NO:14)
MRSPVFTDNSSPPVVPQSFQVAHLHAPTGSGKSTKVPAAYAAQGYKVLVLNPSVAATLGFGAYMSKAHGI
DPNIRTGVRTITTGSPITYSTYGKFLADGGCSGGAYDIIICDECHSTDATSILGIGTVLDQAETAGARLV
VLATATPPGSVTGSGSGHHHHHH

NS3- (DeltaN15) (Amino Acids 1205-1658)

FIG. 2A. NS3h(ΔN15) Nucleic Acid Sequence (SEQ ID NO:4)

atgcgttctccggttttcactgacaactcttctccgccggttgttccgcagtcttttccaggttg
ctcacctgcatgctccgactggttctggtaaatctactaaagttccagctgcttacgctgctca
gggttacaaagttctggttctgaacccgtctgttgctgctactctgggtttcggcgcctacatg
tctaaagctcacggtatcgacccgaacattcgtactggtgtacgtactatcactactggttctc
cgatcacttactctacttacggtaaattcctggctgacggtggttgctctggtggtgcttacga
tatcatcatctgcgacgaatgccactctactgacgctacttctatcctgggtatcggtaccgtt
ctggaccaggctgaaactgcaggtgctcgtctggttgttctggctactgctactccgccgggtt
ctgttactgttccgcaccgaacatcgaagaagttgctctgtcgactactggtgaaatcccgtt
ctacggtaaagctatcccgctcgaggttatcaaaggtggtcgtcacctgattttctgccactct
aaaaaaaaatgcgacgaactggctgctaagcttgttgctctgggtatcaacgctgttgcttact
accgtggtctggacgtttctgttatcccgacttctggtgacgttgttgttgtggccactgacgc
tctgatgactggttacactggtgacttcgactctgttatcgattgcaacacttgcgttactcag
accgtagattttagcctggacccgactttcactatcgaaacgatcaccctgccgcaggatgcag
tttcccgtacccagcgtcgtggccgtaccggtcgcggcaaaccgggtatttaccgtttcgtggc
gccgggcgagcgtccatccggtatgttcgatagctctgttctgtgtgagtgttatgacgcggt
tgcgcgtggtacgaactgactccggctgaaactactgtacgcctgcgtgcatacatgaatacgc
cgggtctgccggtgtgtcaagaccacctggaattttgggaaggtgtcttactggcctgaccca
tatcgacgcacactttctgtcccagactaaacagtctggtgaaaacctgccgtacctggtggcg
tatcaagccactgtgtgcgcccgtgcgcaggcgccgccaccgagctgggaccaaatgtggaagt
gcctgatccgtctgaaaccgaccctgcacggtccgacgccactgctgtaccgcctgggtgcagt
gcagaacgaaatcacgctgacgcacccggtcactaaatacattatgacttgcatgagcgcagac
ctggaaggtggcggtctg

FIG. 2B. NS3h(ΔN15) Amino Acid Sequence (SEQ ID NO:5)

MRSPVFTDNSSPPVVPQSFQVAHLHAPTGSGKSTKVPAAYAAQGYKVLVLNPSVAATLGFGAYM
SKAHGIDPNIRTGVRTITTGSPITYSTYGKFLADGGCSGGAYDIIICDECHSTDATSILGIGTV
LDQAETAGARLVVLATATPPGSVTVPHPNIEEVALSTTGEIPFYGKAIPLEVIKGGRHLIFCHS
KKKCDELAAKLVALGINAVAYYRGLDVSVIPTSGDVVVVATDALMTGYTGDFDSVIDCNTCVTQ
TVDFSLDPTFTIETITLPQDAVSRTQRRGRTGRGKPGIYRFVAPGERPSGMFDSSVLCECYDAG
CAWYELTPAETTVRLRAYMNTPGLPVCQDHLEFWEGVFTGLTHIDAHFLSQTKQSGENLPYLVA
YQATVCARAQAPPPSWDQMWKCLIRLKPTLHGPTPLLYRLGAVQNEITLTHPVTKYIMTCMSAD
LE

FIG. 2C. NS3h(ΔN15)-Cbt(v2e) Nucleic Acid Sequence (SEQ ID NO:6)

atgcgttctccggttttcactgacaactcttctccgccggttgttccgcagtctttccaggttg
ctcacctgcatgctccgactggttctggtaaatctactaaagttccagctgcttacgctgctca
gggttacaaagttctggttctgaacccgtctgttgctgctactctgggtttcggcgcctacatg
tctaaagctcacggtatcgacccgaacattcgtactggtgtacgtactatcactactggttctc
cgatcacttactctacttacggtaaattcctggctgacggtggttgctctggtggtgcttacga
tatcatcatctgcgacgaatgccactctactgacgctacttctatcctgggtatcggtaccgtt
ctggaccaggctgaaactgcaggtgctcgtctggttgttctggctactgctactccgccgggtt
ctgttactgttccgcacccgaacatcgaagaagttgctctgtcgactactggtgaaatcccgtt
ctacggtaaagctatcccgctcgaggttatcaaaggtggtcgtcacctgattttctgccactct
aaaaaaaaatgcgacgaactggctgctaagcttgttgctctgggtatcaacgctgttgcttact
accgtggtctggacgtttctgttatcccgacttctggtgacgttgttgttgtggccactgacgc
tctgatgactggttacactggtgacttcgactctgttatcgattgcaacacttgcgttactcag
accgtagattttagcctggacccgactttcactatcgaaacgatcaccctgccgcaggatgcag
tttcccgtacccagcgtcgtggccgtaccggtcgcggcaaaccgggtatttaccgtttcgtggc
gccgggcgagcgtccatccggtatgttcgatagctctgttctgtgtgagtgttatgacgcgggt
tgcgcgtggtacgaactgactccggctgaaactactgtacgcctgcgtgcatacatgaatacgc
cgggtctgccggtgtgtcaagaccacctggaattttgggaaggtgtctttactggcctgaccca
tatcgacgcacactttctgtcccagactaaacagtctggtgaaaacctgccgtacctggtggcg
tatcaagccactgtgtgcgcccgtgcgcaggcgccgccaccgagctgggaccaaatgtggaagt
gcctgatccgtctgaaaccgaccctgcacggtccgacgccactgctgtaccgcctgggtgcagt
gcagaacgaaatcacgctgacgcacccggtcactaaatacattatgacttgcatgagcgcagac
ctggaaggtggcggtctgaacgacatcttcgaggctcagaaaatcgaatggcacgaaggtcatc
atcaccatcaccat

FIG. 2D. NS3h(ΔN15)-Cbt(v2e) Amino Acid Sequence (SEQ ID NO:7)

MRSPVFTDNSSPPVVPQSFQVAHLHAPTGSGKSTKVPAAYAAQGYKVLVLNPSVAATLGFGAYM
SKAHGIDPNIRTGVRTITTGSPITYSTYGKFLADGGCSGGAYDIIICDECHSTDATSILGIGTV
LDQAETAGARLVVLATATPPGSVTVPHPNIEEVALSTTGEIPFYGKAIPLEVIKGGRHLIFCHS
KKKCDELAAKLVALGINAVAYYRGLDVSVIPTSGDVVVVATDALMTGYTGDFDSVIDCNTCVTQ
TVDFSLDPTFTIETITLPQDAVSRTQRRGRTGRGKPGIYRFVAPGERPSGMFDSSVLCECYDAG
CAWYELTPAETTVRLRAYMNTPGLPVCQDHLEFWEGVFTGLTHIDAHFLSQTKQSGENLPYLVA
YQATVCARAQAPPPSWDQMWKCLIRLKPTLHGPTPLLYRLGAVQNEITLTHPVTKYIMTCMSAD
LEGGGLNDIFEAQKIEWHEGHHHHHH

FIG. 2E. NS3h(ΔN15)-XC9 Nucleic Acid Sequence (SEQ ID NO:8)

```
atgcgttctccggttttcactgacaactcttctccgccggttgttccgcagtcttccaggttg
ctcacctgcatgctccgactggttctggtaaatctactaaagttccagctgcttacgctgctca
gggttacaaagttctggttctgaacccgtctgttgctgctactctgggtttcggcgcctacatg
tctaaagctcacggtatcgacccgaacattcgtactggtgtacgtactatcactactggttctc
cgatcacttactctacttacggtaaattcctggctgacggtggttgctctggtggtgcttacga
tatcatcatctgcgacgaatgccactctactgacgctacttctatcctgggtatcggtaccgtt
ctggaccaggctgaaactgcaggtgctcgtctggttgttctggctactgctactccgccgggtt
ctgttactgttccgcacccgaacatcgaagaagttgctctgtcgactactggtgaaatcccgtt
ctacggtaaagctatcccgctcgaggttatcaaggtggtcgtcacctgattttctgccactct
aaaaaaaaatgcgacgaactggctgctaagcttgttgctctgggtatcaacgctgttgcttact
accgtggtctggacgtttctgttatcccgacttctggtgacgttgttgttgtggccactgacgc
tctgatgactggttacactggtgacttcgactctgttatcgattgcaacacttgcgttactcag
accgtagattttagcctggacccgactttcactatcgaaacgatcaccctgccgcaggatgcag
tttcccgtacccagcgtcgtggccgtaccggtcgcggcaaaccgggtatttaccgtttcgtggc
gccgggcgagcgtccatccggtatgttcgatagctctgttctgtgtgagtgttatgacgcggt
tgcgcgtggtacgaactgactccggctgaaactactgtacgcctgcgtgcatacatgaatacgc
cgggtctgccggtgtgtcaagaccacctggaattttgggaaggtgtctttactggcctgaccca
tatcgacgcacactttctgtcccagactaaacagtctggtgaaaacctgccgtacctggtggcg
tatcaagccactgtgtgcgcccgtgcgcaggcgccgccaccgagctgggaccaaatgtggaagt
gcctgatccgtctgaaaccgaccctgcacggtccgacgccactgctgtaccgccttggtgcagt
gcagaacgaaatcacgctgacccatccggtcactaaatacattatgacttgcatgagcgcagac
ctggaaaacaacaacaacaataacaataacaacaacgatgaatgtcatgccgcggatagaggcg
gctgcggtcatcatcaccatcaccat
```

FIG. 2F. NS3h(ΔN15)-XC9 Amino Acid Sequence (SEQ ID NO:9)

```
MRSPVFTDNSSPPVVPQSFQVAHLHAPTGSGKSTKVPAAYAAQGYKVLVLNPSVAATLGFGAYM
SKAHGIDPNIRTGVRTITTGSPITYSTYGKFLADGGCSGGAYDIIICDECHSTDATSILGIGTV
LDQAETAGARLVVLATATPPGSVTVPHPNIEEVALSTTGEIPFYGKAIPLEVIKGGRHLIFCHS
KKKCDELAAKLVALGINAVAYYRGLDVSVIPTSGDVVVVATDALMTGYTGDFDSVIDCNTCVTQ
TVDFSLDPTFTIETITLPQDAVSRTQRRGRTGRGKPGIYRFVAPGERPSGMFDSSVLCECYDAG
CAWYELTPAETTVRLRAYMNTPGLPVCQDHLEFWEGVFTGLTHIDAHFLSQTKQSGENLPYLVA
YQATVCARAQAPPPSWDQMWKCLIRLKPTLHGPTPLLYRLGAVQNEITLTHPVTKYIMTCMSAD
LENNNNNNNNNNDECHAADRGGCGHHHHHH
```

9NB45H - Fusion of Amino Acids 1192-1457, 1-150, and GSGSHHHHHH

FIG. 3A. 9NB45H (Nucleic Acid Sequence) (SEQ ID NO:10)

```
atggctgttgactttatcccggttgaaaatctcgagactactatgcgttctccggttttcactg
acaactcttctccgccggttgttccgcagtctttccaggttgctcacctgcatgctccgactgg
ttctggtaaatctactaaagttccagctgcttacgctgctcagggttacaaagttctggttctg
aacccgtctgttgctgctactctgggtttcggcgcctacatgtctaaagctcacggtatcgac
cgaacattcgtactggtgtacgtactatcactactggttctccgatcacttactctacttacgg
taaattcctggctgacggtggttgctctggtggtgcttacgatatcatcatctgcgacgaatgc
cactctactgacgctacttctatcctgggtatcggtaccgttctggaccaggctgaaactgcag
gtgctcgtctggttgttctggctactgctactccgccgggttctgttactgttccgcacccgaa
catcgaagaagttgctctgtcgactactggtgaaatcccgttctacggtaaagctatcccgctc
gaggttatcaaaggtggtcgtcacctgattttctgccactctaaaaaaaatgcgacgaactgg
ctgctaagcttgttgctctgggtatcaacgctgttgcttactaccgtggtctggacgtttctgt
tatcccgacttctggtgacgttgttgttgtggccactgacgctctgatgactggttacactggt
gacttcgactctgttatcgattgcaacacttgcaattccatgtctaccaacccgaaaccgcaga
aaaaaaacaaacgtaacaccaaccgtcgtccgcaggacgttaaattcccgggtggtggtcagat
cgttggtggtgtttacctgctgccgcgtcgtggtccgcgtctgggtgttcgtgctacgcgtaaa
acctctgaacgttctcagccgcgtgggcgtcgtcagccgatcccgaaagctcgtcgtccggaag
gtcgtacctgggctcagccgggttaccgtggccgctgtacggtaacgaaggttgcggttgggc
tggttggctgctgtctccgcgtggatctcgtccgtcttggggtccgaccgacccgcgtcgtcgt
tctcgtaaccttggtaaagttatcgatacccctgacctgcggtttcgctgacctgatgggttaca
taccgctggttggagctccgctgggtggtgctgctcgtgctggttctggcagccatcatcacca
tcaccat
```

FIG. 3B. 9NB45H (Amino Acid Sequence) (SEQ ID NO:11)

<u>M</u>AVDFIPVENLETTMRSPVFTDNSSPPVVPQSFQVAHLHAPTGSGKSTKVPAAYAAQGYKVLVL
NPSVAATLGFGAYMSKAHGIDPNIRTGVRTITTGSPITYSTYGKFLADGGCSGGAYDIIICDEC
HSTDATSILGIGTVLDQAETAGARLVVLATATPPGSVTVPHPNIEEVALSTTGEIPFYGKAIPL
EVIKGGRHLIFCHSKKKCDELAAKLVALGINAVAYYRGLDVSVIPTSGDVVVVATDALMTGYTG
DFDSVIDCNTC<u>NSMS</u>TNPKPQKKNKRNTNRRPQDVKFPGGGQIVGGVYLLPRRGPRLGVRATRK
TSERSQPRGRRQPIPKARRPEGRTWAQPGYPWPLYGNEGCGWAGWLLSPRGSRPSWGPTDPRRR
SRNLGKVIDTLTCGFADLMGYIPLVGAPLGGAARA<u>GSGSHHHHHH</u>

FIG. 4

Core Peptide: Amino Acids 15-68 with deletions at 34 and 48.

SEQ ID NO:12:

TNRRPQDVKFPGGGQIVGGYLLPRRGPRLGVRTRKTSERSQPRGRRQPIPKA

FIG. 5 (cont.)

```
                                    1401                                                          1457                                                1500
          P26664             (1401) DELAAKLVALGINAVAYYRGLDVSVIPTSGDVVVVATDALMTGYTGDFDSVIDCNTCVTQTVDFSLDPTFTIETITLPQDAVSRTQRRGRTGRGKPGIYR
NS3h(delN15)-Cbt(v2e)         (197) DELAAKLVALGINAVAYYRGLDVSVIPTSGDVVVVATDALMTGYTGDFDSVIDCNTCVTQTVDFSLDPTFTIETITLPQDAVSRTQRRGRTGRGKPGIYR
   NS3h(delN15)-XC9           (197) DELAAKLVALGINAVAYYRGLDVSVIPTSGDVVVVATDALMTGYTGDFDSVIDCNTCVTQTVDFSLDPTFTIETITLPQDAVSRTQRRGRTGRGKPGIYR
NS3h(d1,delN15)-Cbt(v2e)      (177) -----------------------------------------------------------------------------------------------------
NS3h(d1,delN15)-XC9           (181) -----------------------------------------------------------------------------------------------------
           45H                (211) DELAAKLVALGINAVAYYRGLDVSVIPTSGDVVVVATDALMTGYTGDFDSVIDCNTCNS(insert core 1-150 here)------------------
        NS3h(d1)              (178) -----------------------------------------------------------------------------------------------------
     NS3h(d1)-Cbt             (195) -----------------------------------------------------------------------------------------------------
   NS3h(d1, delN15)           (164) -----------------------------------------------------------------------------------------------------
         Consensus           (1401)

Domain 3
                                    1501            1512                                                                                 1600
          P26664             (1501) FVAPGERPSGMFDSSVLCECYDAGCAWYELTPAETVRLRAYMNTPGLPVCQDHLEFWEGVFTGLTHIDAHFLSQTKQSGENLPYLVAYQATVCARAQAP
NS3h(delN15)-Cbt(v2e)         (297) FVAPGERPSGMFDSSVLCECYDAGCAWYELTPAETVRLRAYMNTPGLPVCQDHLEFWEGVFTGLTHIDAHFLSQTKQSGENLPYLVAYQATVCARAQAP
   NS3h(delN15)-XC9           (297) FVAPGERPSGMFDSSVLCECYDAGCAWYELTPAETVRLRAYMNTPGLPVCQDHLEFWEGVFTGLTHIDAHFLSQTKQSGENLPYLVAYQATVCARAQAP
NS3h(d1,delN15)-Cbt(v2e)      (177) -----------------------------------------------------------------------------------------------------
NS3h(d1,delN15)-XC9           (181) -----------------------------------------------------------------------------------------------------
           45H                (306) -----------------------------------------------------------------------------------------------------
        NS3h(d1)              (178) -----------------------------------------------------------------------------------------------------
     NS3h(d1)-Cbt             (195) -----------------------------------------------------------------------------------------------------
   NS3h(d1, delN15)           (164) -----------------------------------------------------------------------------------------------------
         Consensus           (1501)

1654  1658
                                    1601                                                                                                   1700
          P26664             (1601) PPSWDQMWKCLIRLKPTLHGPTPLLYRLGAVQNEITLTHPVTKYIMTCMSADLEVTSTWVLVGGVLAALAAYCLSTGCVVLVGRVVLSGKPAIIPDREV
NS3h(delN15)-Cbt(v2e)         (397) PPSWDQMWKCLIRLKPTLHGPTPLLYRLGAVQNEITLTHPVTKYIMTCMSADLEGGGLNDIFEAQKIEWHEGHHHHHH---------------------
   NS3h(delN15)-XC9           (397) PPSWDQMWKCLIRLKPTLHGPTPLLYRLGAVQNEITLTHPVTKYIMTCMSADLENNNNNNNNDECHAADRGGCGHHHHHH---------------------
NS3h(d1,delN15)-Cbt(v2e)      (177) -----------------------------------------------------------------------------------------------------
NS3h(d1,delN15)-XC9           (181) -----------------------------------------------------------------------------------------------------
           45H                (406) -----------------------------------------------------------------------------------------------------
        NS3h(d1)              (178) -----------------------------------------------------------------------------------------------------
     NS3h(d1)-Cbt             (195) -----------------------------------------------------------------------------------------------------
   NS3h(d1, delN15)           (164) -----------------------------------------------------------------------------------------------------
         Consensus           (1601)
```

33c (aka 9NB49): Amino Acids 1192-1457

FIG. 6A. 33C Nucleic acid Sequence (SEQ ID NO:15)

gctgttgactttatcccggttgaaaatctcgagactactatgcgttctccggttttcactgacaactcttctccgccggttgttccgcagtctttccaggttg
ctcacctgcatgctccgactggttctggtaaatctactaaagttccagctgcttacgctgctcagggttacaaagttctggttctgaacccgtctgttgctg
ctactctgggtttcggcgcctacatgtctaaagctcacggtatcgacccgaacattcgtactggtgtacgtactatcactactggttctccgatcacttact
ctacttacggtaaattcctggctgacggtggttgctctggtggtgcttacgatatcatcatctgcgacgaatgccactctactgacgctacttctatcctgg
gtatcggtaccgttctggaccaggctgaaactgcaggtgctcgtctggttgttctggctactgctactccgccgggttctgttactgttccgcacccgaac
atcgaagaagttgctctgtcgactactggtgaaatcccgttctacggtaaagctatcccgctcgaggttatcaaaggtggtcgtcacctgattttctgcc
actctaaaaaaaaatgcgacgaactggctgctaagcttgttgctctgggtatcaacgctgttgcttactaccgtggtctggacgtttctgttatcccgact
tctggtgacgttgttgttgtggccactgacgctctgatgactggttacactggtgacttcgactctgttatcgattgcaacacttgc

FIG. 6B. 33C Amino Acid Sequence (SEQ ID NO:16)

AVDFIPVENLETTMRSPVFTDNSSPPVVPQSFQVAHLHAPTGSGKSTKVPAAYAAQGYKVLVLNPSVAATLGFGAYMS
KAHGIDPNIRTGVRTITTGSPITYSTYGKFLADGGCSGGAYDIIICDECHSTDATSILGIGTVLDQAETAGARLVVLATATPP
GSVTVPHPNIEEVALSTTGEIPFYGKAIPLEVIKGGRHLIFCHSKKKCDELAAKLVALGINAVAYYRGLDVSVIPTSGDVVVV
ATDALMTGYTGDFDSVIDCNTC

SUBJECT ANTI-HCV ANTIBODY DETECTION ASSAYS EMPLOYING NS3 CAPTURE PEPTIDES

The present application is a continuation of copending U.S. application Ser. No. 16/122,261, filed Sep. 5, 2018, which is a continuation of U.S. application Ser. No. 14/925,778, filed Oct. 28, 2015, now U.S. Pat. No. 10,088,483, which claims priority to U.S. Provisional Patent Application No. 62/072,266, filed Oct. 29, 2014, each of which is herein incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 53,106 Byte ASCII (Text) file named "34164-304_ST25.TXT," created on Oct. 15, 2020.

FIELD OF THE INVENTION

The present disclosure provides methods, kits, and compositions for detecting subject anti-HCV antibodies in a sample using NS3 capture peptides. In certain embodiments, at least two NS3 helicase (NS3h) capture peptides and at least two conjugate peptides (e.g., NS3h conjugate peptides) are employed together, which allows for a broad dynamic range of subject antibody detection in a one-step type assay. In other embodiments, methods are provided of detecting NS3-specific subject antibodies without the use of a reducing agent. In some embodiments, NS3-specific subject antibodies are detected with a 'double shot' of NS3 conjugate peptide (e.g., conjugate peptide added to a sample both before and after washing).

BACKGROUND

According to WHO statistics, as many as 170 million people worldwide are infected by hepatitis C virus (HCV), a viral infection of the liver. 75 to 85% of persons infected with HCV progress to chronic infection, approximately 20% of these cases develop complications of chronic hepatitis C, including cirrhosis of the liver or hepatocellular carcinoma after 20 years of infection. The current recommended treatment for HCV infections is a combination of interferon and ribavirin drugs, however the treatment is not effective in all cases and the liver transplantation is indicated in hepatitis C-related end-stage liver disease. At present, there is no vaccine available to prevent HCV infection, therefore all precautions to avoid infection must be taken. Therefore, sensitive HCV detection assays are important for public safety.

SUMMARY OF THE INVENTION

The present disclosure provides methods, kits, and compositions for detecting subject anti-HCV antibodies in a sample using NS3 capture peptides. In certain embodiments, at least two NS3 helicase (NS3h) capture peptides and at least two conjugate peptides (e.g., NS3h conjugate peptides) are employed together, which allows for a broad dynamic range of subject antibody detection in a one-step type assay. In other embodiments, methods are provided of detecting NS3-specific subject antibodies without the use of a reducing agent. In some embodiments, NS3-specific subject antibodies are detected with a 'double shot' of NS3 conjugate peptide (e.g., conjugate peptide added to a sample both before and after washing).

In some embodiments, provided herein are methods of detecting hepatitis C virus (HCV) infection in a subject comprising: a) contacting an initial biological sample (e.g., blood, plasma, serum, semen, etc.) with first and second NS3h (NS3 helicase) capture peptides and first and second detectably labeled conjugate peptides (e.g., NS3h specific conjugate peptides) to generate a mixed biological that comprises the initial biological sample, the first and second NS3h capture peptides, and the first and second conjugate peptides, wherein the first and second NS3h capture peptides: i) each comprise an amino acid sequence encoding at least one HCV NS3 helicase epitope; and ii) have different amino acid sequences (e.g., have at least one amino acid difference, such as a difference in length or sequence), wherein the initial biological sample is suspected of containing subject antibodies, and wherein the subject antibodies are not in purified form in the biological sample, b) incubating the mixed biological sample under conditions such that: the first NS3h capture peptide specifically binds at least one of the subject antibodies to form a first capture complex and the first (or second) conjugate peptide binds the subject antibody in the first capture complex to form a first detectable complex, and the second NS3h capture peptide specifically binds at least one of the subject antibodies to form a second capture complex and the second (or first) conjugate peptide binds the subject antibody in the second capture complex to form a second detectable complex; c) washing the mixed biological sample to generate a washed sample; and d) detecting the presence of the first and/or second detectable complexes, thereby detecting the presence of past or present HCV infection in the subject, wherein the presence of both the first and second NS3h capture peptides in the mixed biological sample extends the dynamic range for detecting (e.g., qualitatively or quantitatively) the subject antibodies compared to only using the first or second NS3h capture peptide.

In certain embodiments, the present disclosure provides kits or systems comprising: a) first and second NS3h capture peptides, wherein the first and second NS3h capture peptides: i) each comprise an amino acid sequence encoding at least one HCV NS3 helicase epitope; ii) have different amino acid sequences, iii) are able to bind to at least one subject antibody in a biological sample for form capture complexes, and b) first and second conjugate peptides, wherein the first and second conjugate peptides are able to bind to the subject antibodies in the capture complexes. In certain embodiments, the kits and systems further comprise: c) the biological sample containing the subject antibodies, and wherein the subject antibodies are not in purified form in the biological sample.

In further embodiments, provided herein are compositions comprising: a) first and second NS3h capture peptides, wherein the first and second NS3h capture peptides: i) each comprise an amino acid sequence encoding at least one HCV NS3 helicase epitope; ii) have different amino acid sequences, iii) are able to bind to at least one subject antibody in a biological sample for form capture complexes, and b) first and second conjugate peptides, wherein the first and second conjugate peptides are able to bind to the subject antibodies in the capture complexes. In certain embodiments, compositions further comprise c) the biological sample containing the subject antibodies, and wherein the subject antibodies are not in purified form in the biological sample. In other embodiments, the compositions are free or detectably free of detergents.

In particular embodiments, provided herein are methods of detecting hepatitis C virus (HCV) infection in a subject comprising: a) contacting a sample suspected of containing subject antibodies with: i) a first NS3h capture peptide comprising an amino acid sequence with at least 80% or 90% sequence identity (e.g., at least 80% . . . 90% . . . 95% . . . 98% . . . 99.5% . . . or 100% sequence identity) with Domain 1 and/or Domain 2 of an HCV NS3 helicase, wherein the first NS3h capture peptide is no more than 400 or 350 or 300 amino acids in length (e.g., no more than 400 . . . 375 . . . 325 . . . 300 . . . 275 . . . 250 . . . 225 . . . 200 . . . or 180 amino acids in length); ii) a second NS3h capture peptide which comprises an amino acid sequence with at least 85% or 90% or 95% (e.g., at least 85% . . . 90% . . . 94% . . . 97% . . . 99% . . . 99.5% . . . 99.9% . . . or 100%) sequence identity with a full-length HCV NS3 helicase that comprises Domains 1, 2, and 3 of an HCV NS3 helicase, and b) incubating the sample under conditions such that the first NS3h capture peptide specifically binds at least one of the subject antibodies to form a first complex, and the second NS3h capture peptide specifically binds at least one of the subject antibodies to form a second complex; and c) detecting the presence of the first and/or second complex, thereby detecting the presence of past or present HCV infection in the subject. In particular embodiments, the presence of the first NS3h capture peptide along with the second NS3h capture peptide in the sample extends the upper dynamic range for qualitatively detecting the subject antibodies compared to only using the second NS3h peptide.

In certain embodiments, provided herein are kits and systems comprising: a) a first NS3h capture peptide comprising an amino acid sequence with at least 80% or 90% sequence identity with Domain 1 and/or Domain 2 of an HCV NS3 helicase, wherein the first NS3h peptide is no more than 400 or 350 or 300 or 225 amino acids in length; b) a second NS3h capture peptide comprising an amino acid sequence with at least 85% or 95% sequence identity with a full-length HCV NS3 helicase that comprises Domains 1, 2, and 3 of an HCV NS3 helicase.

In certain embodiments, the kits and systems further comprise a first container, wherein the first and second NS3h capture peptides are inside the first container. In other embodiments, the first container is free or substantially free of a detergent. In other embodiments, the kits and systems further comprise a solid support (e.g., microparticles). In other embodiments, the kits and systems further comprise a second container, wherein the solid support is inside the second container. In further embodiments, the kits and systems further comprise a first detectably labeled conjugate peptide (e.g., that will bind to a subject antibody captured by the first or second NS3h capture peptide). In certain embodiments, the first detectably labeled conjugate peptide: i) comprises an amino acid sequence with at least 80% or 90% sequence identity with Domain 1 of an HCV NS3 helicase, ii) is no more than 250 or 200 amino acids in length; and iii) comprises a detectable label. In additional embodiments, the kits and systems further comprise a second detectably labeled conjugate peptide (e.g., that will bind to a subject antibody captured by the first or second NS3h capture peptide). In certain embodiments, the second detectably labeled conjugate peptide: i) comprises an amino acid sequence with at least 80% or 90% sequence identity with a full-length HCV NS3 helicase that has Domains 1, 2, and 3 of an HCV NS3 helicase, and ii) comprises a detectable label. In some embodiments, the kits and systems further comprise a second (or third) container, wherein the first and second NS3h conjugate peptides are inside the second (or third) container. In particular embodiments, the second container is free or substantially free of detergent.

In certain embodiments, the kits and systems further comprise a first anti-HCV antibody. In some embodiments, the first anti-HCV antibody is an anti-core HCV antibody or anti-NS3 or NS4 antibody. In other embodiments, the first anti-HCV antibody comprises a solid-support binding moiety. In further embodiments, the kits and systems further comprises a second anti-HCV antibody. In certain embodiments, the second anti-HCV antibody is an anti-core HCV antibody. In some embodiments, the kits and systems further comprise a second container, wherein the second anti-HCV antibody is inside the second container. In certain embodiments, the kits and systems further comprise an HCV core capture peptide. In additional embodiments, the HCV core capture peptide comprises a solid-support binding moiety. In other embodiments, the kits and systems further comprise an HCV detectably labeled conjugate core peptide.

In certain embodiments, the present disclosure provides compositions comprising: a) a first NS3h capture peptide comprising an amino acid sequence with at least 80% or 90% (e.g., 80% . . . 90% . . . 95% . . . 99% . . . 99.5%) sequence identity with Domain 1 and/or Domain 2 of an HCV NS3 helicase, wherein the first NS3h peptide is no more than 250 or 350 amino acids in length (e.g., no more than 250 . . . 300 . . . or 350); and b) a second NS3h capture peptide comprising an amino acid sequence with at least 90% or 95% sequence identity with a full-length HCV NS3 helicase that comprises Domains 1, 2, and 3 of an HCV NS3 helicase. In some embodiments, the compositions further comprise at least one of the following components: c) a solid support; d) a first detectably labeled conjugate peptide; e) a second detectably labeled conjugate peptide; f) a first anti-HCV antibody; g) a second anti-HCV antibody which is detectably labeled; h) an HCV core capture peptide; and i) a detectably labeled HCV core conjugate peptide. In particular embodiments, the composition has at least two, three, four, five, six, or all seven of the components.

In certain embodiments, provided herein are compositions comprising at least one peptide comprising or consisting of the amino acid sequence in any one of SEQ ID NOs:1-16, or a peptide with at least 95% (e.g., 95% . . . 98% . . . 99% . . . or 99.5%) sequence identity with any one of SEQ ID NOs:1-16.

In some embodiments, provided herein are methods of detecting hepatitis C virus (HCV) infection in a subject comprising: a) contacting a sample suspected of containing subject antibodies with an NS3 capture peptide, wherein the NS3 capture peptide comprises an amino acid sequence encoding at least one HCV NS3 epitope, and wherein the contacting is conducted under conditions such that no exogenous reducing agent (i.e., a reducing agent not naturally present in the sample) is added to, or present in, the sample, b) incubating the sample under conditions such that the NS3 capture peptide specifically binds at least one of the subject antibodies to form a first complex, wherein the incubating is conducted under conditions wherein no exogenous reducing agent is present in the sample; and c) detecting the presence of the first complex, thereby detecting the presence of past or present HCV infection in the subject, wherein the detecting is conducted under condition wherein no exogenous reducing agent is present.

In certain embodiments, provided herein are kits, systems, and compositions comprising: a composition comprising a biological sample, an NS3 capture peptide, a detectably labeled conjugate peptide, and a plurality of subject antibodies, wherein the NS3 capture peptide and the conjugate peptide are bound to at least one subject antibody, and wherein the composition is free from exogenous reducing agents.

In some embodiments, provided herein are methods of detecting hepatitis C virus (HCV) infection in a subject comprising: a) contacting an initial biological sample with a first NS3 capture peptide and a first conjugate peptide to generate a mixed biological that comprises the initial biological sample, the first NS3 capture peptide and the first conjugate peptides, wherein the NS3 capture peptide comprises an amino acid sequence encoding at least one HCV NS3 helicase epitope; wherein the initial biological sample is suspected of containing subject antibodies, and wherein the subject antibodies are not in purified form in the biological sample, b) incubating the mixed biological sample under conditions such that the NS3 capture peptide specifically binds at least one of the subject antibodies to form a capture complex and the conjugate peptide binds the subject antibody in the capture complex to form a detectable complex, and c) washing the mixed biological sample to generate a washed sample; d) adding additional amounts of the conjugate peptide or a different conjugate peptide that specifically binds the subject antibody in the capture complex; and e) detecting the presence of the detectable complex, thereby detecting the presence of past or present HCV infection in the subject. In further embodiments, the conjugate peptide binds to at least one epitope of NS3h (NS3h helicase of HCV).

In certain embodiments, the amino acid sequence of the second NS3h capture peptide is at least 1.5 or 2 times longer than the first NS3h capture peptide (e.g., at least 1.5 . . . 3.0 . . . 4.0 . . . 5.0 times longer or more). In some embodiments, the first and second conjugate epitopes are specific for an NS3h epitope. In further embodiments, the first NS3h capture peptide has at least 80% or 90% (e.g., 80% . . . 87% . . . 94% . . . 98% . . . 99%, . . . or 95.5%) sequence identity with an HCV NS3 helicase Domain 1, and is no more than 250 amino acids in length. In further embodiments, the first NS3h capture peptide has at least 80 or 90% sequence identity with an HCV NS3 helicase Domain 2, and is no more than 250 amino acids in length (e.g., no more than 250 . . . 225 . . . 200 . . . or 180 amino acids in length). In additional embodiments, the second NS3h capture peptide has at least 90% or 95% (e.g., 90% . . . 94% . . . 96% . . . or 99%) sequence identity with a full-length NS3 helicase having Domains 1, 2, and 3. In certain embodiments, the second NS3h capture peptide comprises a full-length NS3 helicase sequence having Domains 1, 2, and 3. In further embodiments, the amino acid sequence of the second NS3h capture peptide has at least 99% sequence identity with the full-length HCV helicase. In additional embodiments, the amino acid sequence of the second NS3h capture peptide comprises a full-length NS3 helicase sequence having Domains 1, 2, and 3. In further embodiments, the second NS3h capture peptide has a NS3 helicase native structure (i.e., not denatured structure).

In some embodiments, the sample is further suspected of containing HCV particles or fragments thereof, and wherein the method further comprises contacting the sample with a first anti-HCV capture antibody such that a third complex is formed, wherein the third complex comprises the first anti-HCV capture antibody bound to an HCV particle or fragment thereof. In other embodiments, the first capture anti-HCV antibody is an anti-core HCV antibody. In additional embodiment, the first anti-HCV antibody comprises a solid-support binding moiety. In additional embodiments, the methods further comprise contacting the sample with a second anti-HCV antibody (e.g., conjugate antibody) that binds the HCV particle or fragment thereof in the third complex, wherein the second anti-HCV antibody is detectably labeled. In further embodiments, the the second anti-HCV antibody is an anti-core HCV antibody. In some embodiments, the methods further comprise detecting the third complex.

In certain embodiments, prior to any detection by conjugate peptide or conjugate antibody, the sample is washed. In some embodiments, the methods further comprise contacting the sample with a first HCV core peptide (e.g., core capture peptide), wherein the first core peptide specifically binds at least one of the subject antibodies to form a fourth complex. In additional embodiments, the first HCV core peptide comprises or consists of the amino acid sequence shown in SEQ ID NO:12 or one with 95% or more identity with SEQ ID NO:12. In further embodiments, the first HCV core peptide comprises a solid-support binding moiety.

In additional embodiments, provided the methods further comprise contacting the sample with a second HCV core peptide (e.g., conjugate peptide), wherein the second HCV core peptide is detectably labeled, and wherein the second HCV core peptide binds to the subject antibody as part of the fourth complex. In certain embodiments, the methods further comprise detecting the presence of the fourth complex. In additional embodiments, the methods further comprise contacting the sample with a solid support (e.g., microbeads, etc.). In further embodiments, the solid support is coated with avidin or other binding molecule.

In additional embodiments, the methods further comprise contacting the sample with a first detectably labeled conjugate peptide that binds to the subject antibody as part of the first complex, and wherein the detecting the presence of the first complex comprises detecting the first detectably labeled conjugate peptide. In further embodiments, the first detectably labeled conjugate peptide: i) comprises an amino acid sequence with at least 80% . . . 90% . . . or 99% sequence identity with Domain 1 of an HCV NS3 helicase, ii) is no more than 300 . . . 200 . . . or 180 amino acids in length; and iii) comprises a detectable label.

In certain embodiments, the methods further comprise contacting the sample with a second detectably labeled conjugate peptide that binds to the subject antibody as part of the second complex, and wherein the detecting the presence of the second complex comprises detecting the second detectably labeled conjugate peptide. In other embodiments, the second detectably labeled conjugate peptide comprises an amino acid sequence with at least 80% . . . 90% . . . 99% sequence identity with the full-length HCV NS3 helicase. In additional embodiments, the first NS3h capture peptide is no more than 180 amino acids in length. In further embodiments, the first NS3h capture peptide comprises or consists of the amino acid sequence in SEQ ID NO:2 or SEQ ID NO:3, or wherein the first NS3 peptide has 90% . . . or 95% identity with SEQ ID NO:2 or SEQ ID NO:3. In additional embodiments, the first NS3h capture peptide comprises or consists of at least 100 contiguous amino acids (e.g., at least 100 . . . 125 . . . or 135) from SEQ ID NO:2 or SEQ ID NO:3.

In further embodiments, the second NS3h capture peptide has at least 90% . . . or 95% sequence identity with the full-length HCV NS3 helicase. In certain embodiments, the second NS3h capture peptide has at least 99% sequence identity with the full-length HCV NS3 helicase. In other embodiments, the second NS3h capture peptide comprises or consists of the amino acid sequence in SEQ ID NO:5 or SEQ ID NO:7, or wherein the second NS3h capture peptide has 90% . . . or 95% sequence identity with SEQ ID NO:5 or SEQ ID NO:7. In additional embodiments, the second NS3h capture peptide comprises or consists of at least 300 . . . 350 contiguous amino acids from SEQ ID NO:5 or SEQ ID NO:7.

In further embodiments, the first conjugate peptide has at least 90% . . . or 95% identity with Domain 1 of an HCV NS3 helicase. In other embodiments, the first conjugate peptide is no more than 180 amino acids in length. In other embodiments, the first conjugate peptide comprises or consists of the amino acid sequence in SEQ ID NO:2 or SEQ ID NO:3, or wherein the first conjugate peptide has 95% identity with SEQ ID NO:2 or SEQ ID NO:3. In additional embodiments, the second conjugate peptide has at least 95% sequence identity with the full-length HCV NS3 helicase. In other embodiments, the second conjugate peptide has at least 99% sequence identity with the full-length HCV NS3 helicase. In certain embodiments, the second conjugate peptide comprises or consists of the amino acid sequence in SEQ ID NO:5 or SEQ ID NO:7, or wherein the second conjugate peptide has 95% identity with SEQ ID NO:5 or SEQ ID NO:7.

In some embodiments, the Domain 1 of an HCV NS3 helicase is from a HCV genotype selected from the group consisting of: 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a, and 6a. In further embodiments, the full-length HCV NS3 helicase is from a HCV genotype selected from the group consisting of: 1a, 1 b, 2a, 2b, 2c, 2d, 3a, 3b, 3c, 3d, 3e, 3f, 4a, 4b, 4c, 4d, 4e, 4f, 4g, 4h, 4i, 4j, 5a, and 6a. In other embodiments, the subject is a human. In additional embodiments, the solid-support binding moiety comprises biotin. In further embodiments, methods further comprise adding a trigger solution to the sample, wherein the trigger solution triggers a signal from the detectable label.

DESCRIPTION OF THE FIGURES

FIGS. 1A and 1B show the amino acid sequences of exemplary peptide termed NS3-D1, which include amino acids 1192-1356 of HCV according to the standard numbering, which includes all of the helicase Domain 1 (1207-1356), and a small portion of the NS3 protease (119201207). FIG. 1A specifically shows the amino acid sequences of NS3-D1 capture peptide (SEQ ID NO:2) with an N-terminal histidine tag (e.g., for protein purification), while FIG. 1B shows a biotinylated version of NS3-D1 (SEQ ID NO:3) (e.g., such that this peptide can bind to avidin-coated microbeads). FIGS. 1C-E show an exemplary sequence termed "NS3-D1, DelN15," which is amino acids 1205-1356. FIG. 1C specifically shows the amino acid sequence of exemplary peptide NS3-D1, delN15-Cbt (v2e), SEQ ID NO:1, with a biotin sequence at the C-terminus. FIG. 1D specifically shows the amino acid sequence of exemplary peptide NS3-D1, delN15-XC9, SEQ ID NO:13, which has the "XC9" sequence at the C-terminal end, which is designed to bind acridinylated BSA for labeling purposes. FIG. 1E provides the amino acid sequence of NS3-D1, del N15 (SEQ ID NO:14), with an N-terminal histidine tag.

FIGS. 2A-2F show the nucleic acid and amino acid sequences of exemplary NS3h peptides NS3-(DeltaN15) (amino acids 1205-1658) which includes the full-length HCV NS3 helicase with all three domains. FIG. 2A specifically shows the nucleic acid sequence of NS3h(deltaN15) (SEQ ID NO:4). FIG. 2B shows the amino acid sequence of NS3h(deltaN15) (SEQ ID NO:5). FIG. 2C shows the nucleic acid sequence of NS3h(deltaN15)-Cbt(v2e) (SEQ ID NO:6), which encodes a c-terminal biotin tag. FIG. 2D shows the amino acid sequence of NS3h(deltaN15)-Cbt(v2e) (SEQ ID NO:7), which includes a c-terminal biotin tag. FIG. 2E shows the nucleic acid sequence of NS3h(deltaN15)-XC9 (SEQ ID NO:8), which encodes a c-terminal XC9 sequence. FIG. 2F shows the amino acid sequence of NS3h(deltaN15)-XC9 (SEQ ID NO:9), which encodes an XC9 sequence designed to bind acridinylated BSA for labeling purposes.

FIG. 3A shows the nucleic acid sequence (SEQ ID NO:10) of the fusion peptide 9NB45H, and FIG. 3B shows the amino acid sequence (SEQ ID NO:11) of fusion peptide 9NB45H, which is a fusion of amino acids 1192-1457 (NS3 region), 1-150 (core region), and GSGSHHHHHH (histidine tag). This sequence is useful, for example, as a calibrator or control sequence.

FIG. 4 shows the amino acid sequence of an exemplary core peptide (SEQ ID NO:12), which is amino acids 15-68, with a deletion at positions 34 and 48.

FIG. 6A shows the amino acid sequence of peptide 33c (aka 9NB49), which is amino acids 1192-1457, and FIG. 6B shows the corresponding nucleic acid sequence.

DEFINITIONS

Figure 5:
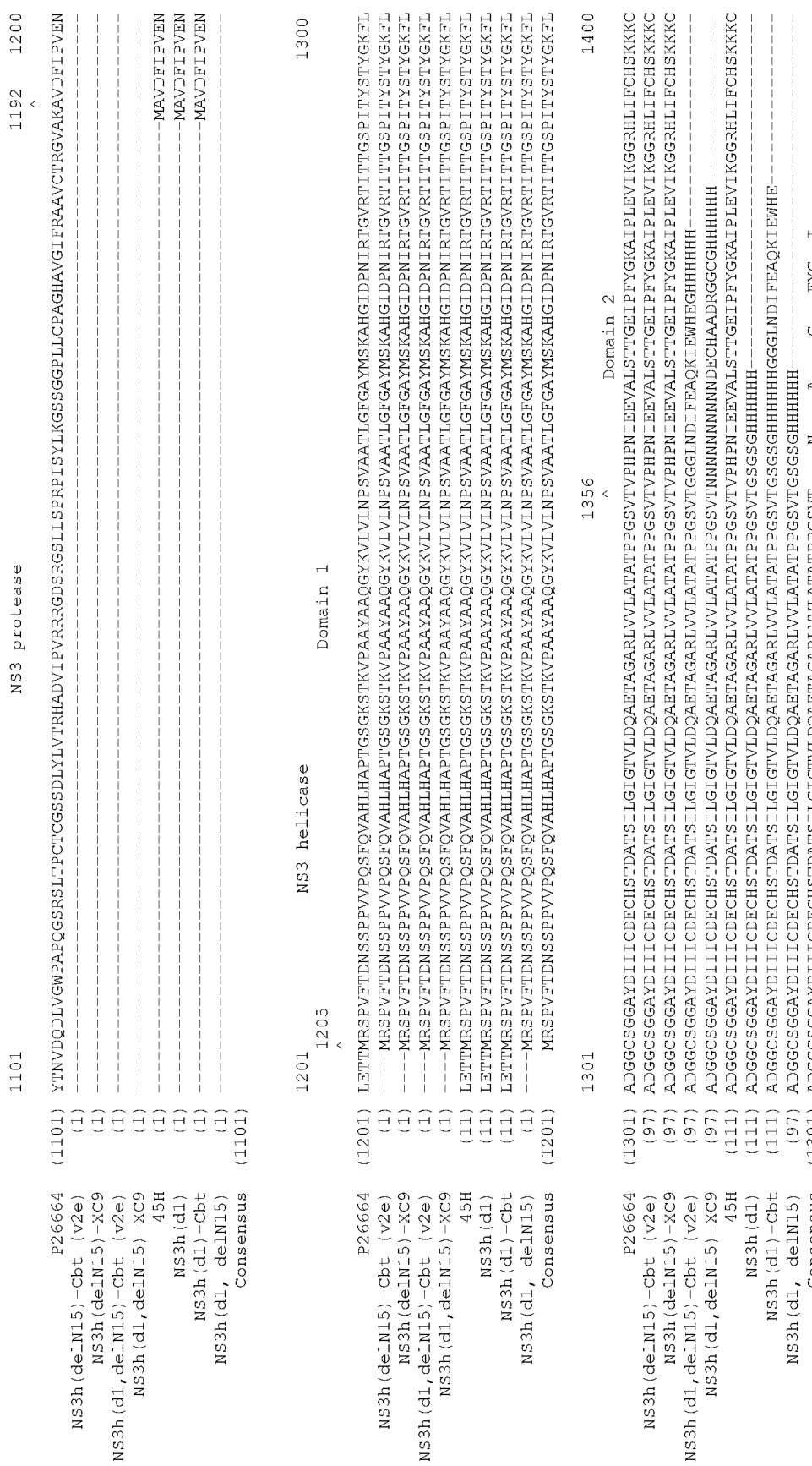
FIG. 5 shows a sequence alignment of the sequences described in FIG. 1-4 and the isolate P26664 in the NS3 region of HCV. This alignment shows a portion of the protease, as well as the location of domains 1, 2, and 3 of the HS3 helicase.

The term "sample," as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood or components thereof), plasma, serum, urine, saliva, amniotic fluid, synovial fluid, endothelial cells, leukocytes, monocytes, other cells, organs, tissues, bone marrow, lymph nodes and spleen.

The term "antibody" (Ab) and "antibodies" (Abs) refer to monoclonal antibodies (mAb (singular) or mAbs (plural)), polyclonal antibodies (pAbs (plural)), multispecific antibodies, human antibodies, humanized antibodies (fully or partially humanized; a polypeptide comprising a modified variable region of a human antibody wherein a portion of the variable region has been substituted by the corresponding sequence from a non-human sequence and wherein the modified variable region is linked to at least part of the constant region of a human antibody), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies (cAb; a polypeptide comprising all or a part of the heavy and light chain variable regions of an antibody from one host species linked to at least part of the antibody constant regions from another host species), single chain antibodies, single domain antibodies, Fab fragments, F(ab') fragments, Fab'-SH fragments, F(ab')2 fragments, Fd fragments, Fv fragments, single-chain Fv fragments ("scFv"), disulfide-linked Fv fragments ("sdFv"), dAb fragments, diabodies, an isolated complementarity determining region (CDR), and anti-idiotypic ("anti-Id") antibodies, bifunctional or dual-domain antibodies (e.g., dual variable domain antibodies, or DVD-IgGs), and functionally active, epitope-binding fragments (or antigenically reactive fragments) of any of the above. In particular, antibodies include immunoglobulin molecules and immunologically active (or antigenically reactive) fragments of immunoglobulin molecules, namely, molecules that contain an analyte-binding site as further described in (n) herein, and variants as further described herein. Immunoglobulin molecules can be of any type (for example, IgG, IgE, IgM, IgD, IgA and IgY), class (for example, IgG1, IgG2, IgG3, IgG4, IgA1 and IgA2), or subclass. An antibody, whose affinity (namely, KD, kd or ka) has been increased or improved via the screening of a combinatory antibody library that has been prepared using bio-display, is referred to as an "affinity maturated antibody." For simplicity sake, an antibody against an analyte is frequently referred to herein as being either an "anti-analyte antibody" or merely an "analyte antibody" (e.g., an anti-HCV antibody or an HCV antibody).

In the present description, the assay "component," "components," and "at least one component," refer to, for example, a capture antibodies, capture peptides (e.g., first and second NS3h capture antibodies), a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide as described herein, which is optionally immobilized on a solid support. Some components can be in solution or lyophilized for reconstitution for use in an assay.

In conducting the assays of the present disclosure, it may be useful to use a control. "Control" refers to a composition known to not contain anti-HCV antibody ("negative control") or to contain anti-HCV antibody ("positive control"). A positive control can comprise a known concentration of anti-HCV antibody. "Control," "positive control," and "calibrator" may be used interchangeably herein to refer to a composition comprising a known concentration of anti-HCV antibody. A "positive control" can be used to establish assay performance characteristics and is a useful indicator of the integrity of reagents (e.g., analytes).

"Epitope," "epitopes" and "epitopes of interest" refer to a site(s) on any molecule (e.g., the NS3 antigens described herein) that is recognized and can bind to a complementary site on a specific binding partner, such as an antibody or antigenically reactive fragment thereof. An epitope is composed of the precise amino acid residues of a region of an antigen (or fragment thereof) known to bind to the complementary site on the specific binding partner. An antigenic fragment can contain more than one epitope. In the assays, kits, and compositions that are described herein, one or other component of the assay may comprise a detectable label. The terms "label" and "detectable label" mean a moiety attached to a specific binding partner, such as an antibody or an analyte, to render the reaction between members of a specific binding pair, such as an antibody and an analyte, detectable, and the specific binding partner, e.g., antibody or analyte, so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

"Linking sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine residues (His tags), such as a 6× His tag, which contains six histidine residues, are useful as linking sequences to facilitate the isolation and purification of polypeptides and antibodies of interest. (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, an mAb, for example, can contain a linking sequence, such as a His tag, an enterokinase cleavage site, or both.

"Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human at risk for HCV infection or a human infected with HCV.

In analysis of the results of the immunoassays described herein it may be useful to include certain levels of detection as cutoff levels. "Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

As described below, it may be desirable in some embodiments to provide a pretreatment of the test sample. "Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., anti-HCV antibody) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

The assays also may be subject to rigorous quality control. "Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

The terms "sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Preferably, the sample is urine, serum or plasma.

In some assays, it may be desirable to provide calibration of the assay. "Series of calibrating compositions" refers to a plurality of compositions comprising a known concentration of anti-HCV antibody, wherein each of the compositions differs from the other compositions in the series by the concentration of anti-HCV antibody.

Throughout the present specification, it is noted that the NS3h antigens and/or other reagents may be bound to a solid support or solid phase, both of which terms are used interchangeably. The term "solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay (e.g., capture on the fly type assays). The solid phase can, for example, be plastic, derivatized plastic, magnetic or non-magnetic metal, glass or silicon, including, for example, a test tube, microtiter well, sheet, beads, microparticles, chip, and other configurations known to those of ordinary skill in the art.

In certain descriptions of the assays, kits, and compositions described herein, it may be useful to refer to either the NS3, NS4 or core antigen or the HCV antibody as a specific binding partner. "Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced. The term "specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to a given antigen (or a fragment thereof) and not bind specifically to other entities.

DETAILED DESCRIPTION

The present disclosure provides methods, kits, and compositions for detecting subject anti-HCV antibodies in a sample using NS3 capture peptides. In certain embodiments, at least two NS3 helicase (NS3h) capture peptides and at least two conjugate peptides (e.g., NS3h conjugate peptides) are employed together, which allows for a broad dynamic range of subject antibody detection in a one-step type assay. In other embodiments, methods are provided of detecting NS3-specific subject antibodies without the use of a reducing agent. In some embodiments, NS3-specific subject antibodies are detected with a 'double shot' of NS3 conjugate peptide (e.g., conjugate peptide added to a sample both before and after washing).

In certain embodiments, the first NS3h capture peptide is composed of substantially only domain 1 of a Hepicavirus (e.g., HCV) NS3 helicase protein (e.g., amino acids 1192-1356 or 1205-1356), while the second NS3h capture peptide is composed of substantially all three domains of the NS3 helicase protein (e.g., amino acids 1207-1654). These two types of proteins may then be added at appropriate levels in a 1-step immunoassay format (both capture and conjugate peptides added at, or about, the same time to a sample prior to any wash) such that samples containing high titer HCV anti-NS3 antibodies are detected by the domain 1 NS3 capture protein and low titer Ab samples are detected by the full-length NS3 helicase peptide. In some embodiments, the first and second NS3h capture peptides contain biotin at the c-terminus (e.g., to bind to avidin coated beads), and a second set of similar or identical proteins are used as conjugate proteins to detect captured antibodies. Such conjugate peptides may be conjugated to acridinylated BSA. In certain embodiments, these four peptides (two capture and two conjugate) are used in a one-step type immunoassay for the detection of antibodies to the HCV NS3 protein.

As shown in Example 1 below, the use of two types of NS3h capture peptides allows for the dynamic range of a 1-step immunoassay for the detection of antibodies to be extended when the two NS3h capture proteins are used in concert. For example, the NS3h domain 1 protein detects samples containing higher concentrations of antibody and the full-length helicase protein detects samples containing lower concentrations of antibody.

In general, 1-step immunoassays tend to have better sensitivity and precision than 2-step assays but the shortfall of the 1-step format is "hook effect." Samples containing high concentrations of analyte in the patient sample overcome the inputs of capture and detection molecules resulting in decreased assay response giving inaccurately low results. In a qualitative assay the decreased result can go below the cutoff resulting in a false negative result. The present disclosure, in certain embodiments, resolves the problem of "hook effect" in a 1-step assay for the detection of antibodies. The present disclosure improves upon what is know, for example, by extending the upper dynamic range of antibody detection by, for example, adding a 2nd protein of lower molecular weight. In particular embodiments, this also simplifies the assay configuration improving the stability in an HCV Ag/Ab Combo format.

In certain embodiments, the methods, kits, and compositions of the present description employ at least first and/or second NS3h capture antibodies. In some embodiments, the NS3h capture peptides have an amino acid sequence comprising or consisting of those shown in FIGS. 1-2 and 5. Variants of these peptides may also be employed that include longer, shorter, or mutated versions of such amino acid sequences (e.g., sequences with 75% . . . 85% . . . 95% . . . or 99% sequence identity with the sequences in these figures or variants thereof). In certain embodiments, the first NS3h capture peptide is composed mainly of only HCV NS3h domain 1, or domain 2, or both domains 1 and 2. It is noted that the generally accepted boundaries of the HCV NS3 helicase are as follows: NS3 helicase Domain 1—aprox. 1207-1356 (181-330); NS3 helicase Domain 2—aprox. 1357-1507 (331-481); and NS3 helicase Domain 3—aprox. 1508-1654 (482-626). In certain embodiments, additional NS3 peptides or variants thereof are provided in U.S. Publ. 20140272933 entitled "HCV Antigen-Antibody Combination Assay and Methods and Compositions for use therein" and U.S. Publication 20140272932 entitled "HCV NS3 Recombinant Antigens and Mutants Thereof for Improved Antibody Detection," both of which are specifically incorporated by reference herein in their entireties, including for the NS3 peptide sequences disclosed therein.

In certain embodiments, the assays described herein further detect the presence of antibodies to Core antigen. Some exemplary core antigens that could be used include antigens derived from the DNA binding domain (amino acids 1-125) of core protein. Still other preferred core antigens are derived from the lipid binding domain of core located at amino acid residues 134-171 of core protein (MGYIPL-VGAPLGGAARALAHGVRVLEDGVNYATGNLPG; SEQ ID NO:17) or from positions 15-68, without or without deletions or other changes (see SEQ ID NO:12, which has deletions at 34 and 48). Thus, the core antigens can be coated onto a solid phase support and/or used in solution phase to capture antibodies present in human serum or plasma that are directed toward the Core region of HCV. Preferably, such core antigens can evade detection by the conjugate antibody used for the detection of Core antigen present in a test sample in an HCV combination immunoassay. Thus a combination immunoassay can be performed that detects both Core antigen present in the test sample at the same time as detecting anti-Core antibodies that would also be expected to be in the test sample and identified in the same HCV Combo assay format.

As noted herein throughout the methods of the present disclosure are generally immunoassay methods. In exemplary embodiments, such methods include methods for isolating a molecule of interest (such as for example a specific antibody that is present in a test sample, or a specific antigen that may be present in the test sample). In order to facilitate such isolation, the molecule of interest, for example, comprises or is attracted to a purification tag that contacts a tag binding partner. The association of the purification tag and the tag binding partner thus may be used to separate the molecule of interest from a mixture of molecules. Purification tags can comprise moieties with the same or similar structures. In certain embodiments, the tagging moiety of an affinity tag can be associated with a functional tag directly by a single bond or via a linkage of stable chemical bonds, in linear, branched or cyclic arrangements, optionally including single, double, triple bond, aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and any combination thereof. In certain embodiments, the association between the tagging moiety and functional tag comprises ether, thioether, carboxamide, sulfonamide, urea or urethane moieties. In certain embodiments, the linkage comprises a polyalkylene chain, i.e., a linear or branched arrangement of carbon-carbon bonds. In other embodiments, the linkage comprises a polyalkylene oxide chain, including a polyethylene glycol moiety. Examples, of affinity tags include, but are not limited to, biotin, digoxigenin (Dig), dinitrophenol (DNP), zinc fingers, fluorinated polymers, and polypeptide sequences such as polyhistidine motifs.

The affinity tags are, in some embodiments, advantageously used to isolate the molecule of interest by relying on the binding or attraction of the affinity tag and a functional group that is attracted to or binds the affinity tag. In some embodiments, solid substrates having an affinity for the tag in that the solid substrate is derivatized with the tag binding partner. In some embodiments, the binding partner may be immobilized on an affinity substrate. The term "affinity substrate" can refer to an immobile matrix or support bound to a binding partner that is capable of forming a strong and preferably reversible interaction with the purification tag of a molecule. An affinity substrate can include a resin, a bead, a particle, a membrane, a gel. The binding partner recognizes or binds to the purification tag specifically. Specific binding partners will depend on the affinity tag, but include charged moieties and one member of a binding pair such as receptor-ligand, antibody-antigen, carbohydrate-lectin, and biotin-streptavidin (or avidin, neutravidin or an anti-biotin antibody).

In specific embodiments, either the C or the N terminus of any or all of the antigens used in the immunoassay may be biotinylated or may comprise a biotin binding moiety (e.g., avidin or streptavidin or neutravidin or an anti-biotin) as the affinity tag. These peptides are biotinylated or avidin/streptavidin-conjugated peptides and will serve as capture antigens. Likewise, the antigens may alternatively be labeled with a detection label in which case they will serve as detection antigens. The detection and capture antigens may have the same underlying amino acid sequence or alternatively, may have different sequences. In exemplary embodiments, the capture antigens are biotinylated at either the C or the N terminus to facilitate binding thereof to solid supports that have the biotin binding partner (i.e., avidin or streptavidin). For exemplary production purposes, the biotinylated peptides are recombinantly expressed in E. coli BL2L(DE3) cells via an IPTG induction system at 25° C. In situ biotinylation at the C-terminal or N-terminal biotinylation is accomplished by co-transformation of the BL21(DE3) cells with the HCV expression plasmid expressing the desired peptide and a second plasmid containing the BirA gene from E. coli (Weiss et al. (1994) Protein Expression & Purif, 14:751-755; Schatz et al. (1993) Biotechnology, 11:1138-1143). Purification of the recombinant proteins is performed using divalent cation chelators that are shown to prevent metal-catalyzed oxidation and aggregation of the protein. Protein stability is significantly improved when EDTA or related divalent cation chelator is added to the buffers used during purification and to the final storage buffer or buffers used in the immunoassay.

In certain embodiments, besides determining the presence of subject antibodies in a sample, the assays also determine the presence of one or more HCV antigens in the sample. In such embodiments, it will be desirable to use monoclonal anti-HCV antibodies to capture the antigen from the test sample and then use further conjugate antibodies to detect the presence of antigen that has been captured. There are numerous commercially available antibodies that may be used in this endeavor. Specifically, such antibodies preferably determine the presence of Core antigen in the test sample. Antibodies directed to Core antigen are known to those of skill in the art include, for example, those described in US Patent Publication No. 20120009196 and 20140272931, both of which are herein incorporated by reference in their entirety.

In specific exemplary embodiments the antibodies used in the combination immunoassay are antibodies designed to detect HCV core protein or fragments thereof in a test sample. Such antibodies may detect the DNA binding domain, the lipid binding domain or the complete Core protein. In some embodiments, the detection antibody used in the immunoassay is directed to the lipid binding domain of core peptide. In still other embodiments, the anti-HCV Core antibodies used in the combination assays may be for example, C11-3, C11-7, C11-9, and C11-14 (as described in U.S. Pat. No. 6,727,092; Morota, et al, J. Virol. Meth., 2009, 157:8-14).

In a specific assay of the present invention, the immunoassay at least detects NS3h specific subject antibodies, core antigen, as well detecting core antibodies in the test sample. In such embodiments, it becomes desirable, although not essential to ensure that the capture antigen that is designed to capture anti-Core one that preferably comprise certain deletions or substitution in the known epitope binding regions for specific monoclonal antibodies such that monoclonal antibodies used for HCV core antigen detection would fail to detect these modified core antigens but would nonetheless detect complete core antigen from the test sample. Exemplary anti-core antibodies to be used as capture antibodies include antibodies AOT3, C11-3, C11-7, C11-9, and C11-14 as described in U.S. Pat. No. 6,727,092 as well as Morota, et al, J. Virol. Meth., 2009, 157:8-14.

In particular embodiments, the antigens and antibodies described herein are contemplated for use as immunodiagnostic reagents in combination immunoassays designed for the detection of multiple HCV components found in a test sample suspected of having been infected with HCV. Immunodiagnostic reagents (be they antibodies or antigens) will be comprised of the herein-described antigen polypeptides and antibodies (typically in combination) such that they can be used in a combination immunoassay designed for the detection of HCV antigens including but not limited to the NS3 region of HCV, the core antigen of HCV, the NS4 region of HCV or combinations thereof as well as anti-HCV antibodies directed against one or more of these regions. For purposes of capture, the antigens and/or antibodies of which the immunodiagnostic reagent is comprised can be coated on a solid support such as for example, a microparticle, (e.g., magnetic particle), bead, test tube, microtiter plate, cuvette, membrane, scaffolding molecule, film, filter paper, disc or chip. In this regard, where the immunodiagnostic reagent comprises a combination of antigens (e.g., directed at different HCV proteins or different fragments of the same HCV protein), the antigens can be co-coated on the same solid support or can be on separate solid supports. Likewise, where the immunodiagnostic reagent comprises one or more antibodies that will be used to capture one or more antigens from the test sample, such antibodies can be co-coated on the same solid support or can be on separate solid supports.

Notably, the immunodiagnostic reagent may be labeled with a detectable label or labeled with a specific partner that allows capture or detection. For example, the labels may be a detectable label, such as a fluorophore, radioactive moiety, enzyme, biotin/avidin label, chromophore, chemiluminescent label, or the like. Such labels are described in further detail infra.

Still further the invention contemplates the preparation of HCV diagnostic kits comprising the immunodiagnostic reagents described herein and may further include instructions for the use of the immunodiagnostic reagents in immunoassays for determining the presence of HCV in a test sample. For example, the kit can comprise instructions for assaying the test sample for anti-HCV antibody (e.g., an anti-NS3h antibody in the test sample) by immunoassay. While certain embodiments employ chemiluminescent microparticle immunoassay for assaying the test sample, it should be understood that the antigens and antibodies used in the immunoassays of the present disclosure may be used in any other immunoassay formats known to those of skill in the art for determining the presence of HCV in a test sample. The instructions can be in paper form or computer-readable form, such as a disk, CD, DVD, or the like. Alternatively or additionally, the kit can comprise a calibrator or control, e.g., purified, and optionally lyophilized, anti-HCV antibody or antigen, and/or at least one container (e.g., tube, microtiter plates or strips, which can be already coated with one or more of the capture components (antigens and/or antibodies) of the combination immunoassay) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. In specific embodiments, it is preferred that all the components are individually presented in the kit such that the immunoassay may be performed as a capture-on-the-fly type immunoassay in which the solid support is coated with an agent that allows binding of the capturing moiety (e.g., a biotinylated antigen or a biotinylated antibody) and the kit further comprises each of the individual capture and detection antigen pairs and the biotinylated capture antibodies in one container and a second container provides the detection antibody conjugate. The instructions for conducting the assay also can include instructions for generating a standard curve or a reference standard for purposes of quantifying anti-HCV antibody.

Any antibodies, which are provided in the kit or systems herein, such as anti-IgG antibodies and anti-IgM antibodies, can also incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates. In one embodiment, there are two containers provided. In the first container is provided at least a first, second and/or third pair of antigens, wherein the first antigen in each pair is a capture antigen from a given HCV protein (e.g., NS3h) that is biotinylated and the second antigen in each pair is a detection antigen from the same protein as the first antigen but is labeled with a detectable label (e.g., it is acridinylated) as well as one or more biotinylated antibodies designed for detecting one or more HCV antigens from a test sample; and in the second container is provided the antibody that forms the conjugation partner for detection of the antigen that is captured by the biotinylated antibodies from the first container. It is contemplated that where there are multiple biotinylated antibodies in the first container, the multiple antibodies that form the conjugation partners may be present in a single container or individual containers for each different antigen detecting conjugate antibody.

In certain embodiments, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kits may also include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit may be provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

In certain embodiments, the detectable label is at least one acridinium compound. In such embodiments, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. It should be understood that in the immunodiagnostic reagent the antigens for antibody detection may be detectably labeled, and any antibodies provided in kit for use along with such reagents also may be detectably labeled.

In certain embodiments, the kit can contain a solid support phase, such as a magnetic particle, bead, test tube, microtiter plate, cuvette, membrane, scaffolding molecule, film, filter paper, disc or chip.

The present disclosure provides immunoassay methods for determining the presence, amount or concentration of anti-HCV antibodies or anti-HCV antibodies and HCV antigens in a test sample. Any suitable assay known in the art can be used in such a method as long as such an assay uses one or more of antigens for detecting HCV antibodies. Examples of such assays include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc.

In particular embodiments, the recombinant antigens (e.g., NS3h antigens) may be used as capture reagents (e.g., by using such antigens in which the amino- or carboxy-terminal of the antigen comprises a biotin tag) or as a detection (conjugate) reagents in which the antigens are either directly or indirectly labeled with acridinium. Indirect labeling may employ the use of acridinylated BSA covalently coupled to the free thiol of unpaired cysteine residues within a protein via SMCC-type linker. To facilitate such indirect labeling certain of the antigens used in the immunoassays of the present disclosure may readily be further modified to include additional cysteine residues at the C-terminus.

Typically, immunoassays are performed in 1-step or 2-step format. Solid phase reagents for capture of immune complexes formed in solution in the 1-step assay include, for example, anti-biotin monoclonal antibody, streptavidin or neutravidin to capture the biotinylated moiety (e.g., a biotinylated antigen for capture of an HCV antibody).

In a SELDI-based immunoassay, a capture reagent that specifically binds anti-HCV-antibody or an HCV antigen is attached to the surface of a mass spectrometry probe, such as a pre-activated protein chip array. The anti-HCV antibody or the antigen is then specifically captured on the biochip, and the captured moiety is detected by mass spectrometry. Alternatively, the anti-HCV antibody can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a particular immunoassay in which a combination of multiple antigens (preferably two or more NS3h antigens) may readily be employed. An agglutination assay, such as a passive hemagglutination assay, also can be used. In an agglutination assay an antigen-antibody reaction is detected by agglutination or clumping. In a passive hemagglutination assay, erythrocytes are coated with the antigen and the coated erythrocytes are used in the agglutination assay.

Methods well-known in the art for collecting, handling and processing urine, blood, serum and plasma, and other body fluids, are used in the practice of the present disclosure, for instance, when the immunodiagnostic reagents comprise multiple antigens and/or in an anti-HCV antibody immunoassay kit. The test sample can comprise further moieties in addition to the polypeptide of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform).

The pretreatment reagent can be any reagent appropriate for use with the immunoassays and kits described herein. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., protein that can bind to anti-HCV antibody or an antigen that can bind to an anti-HCV antibody form the present in the sample). Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for anti-HCV antibody (e.g., an antigen) or the labeled specific binding partner for the HCV antigen (e.g., an antibody). The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 methylene glycol) is still present (or remains) in the test sample mixture during capture.

In a heterogeneous format, after the test sample is obtained from a subject, a first mixture is prepared. The mixture contains the test sample being assessed for anti-HCV antibodies and a first specific capture binding partner, wherein the first specific capture binding partner and any anti-HCV antibodies contained in the test sample form a first specific capture binding partner-anti-HCV antibody complex. The first specific capture binding partner may be an NS3 antigen. Likewise, in the assays provided herein may also contain a second and third specific capture binding partner and these second and third specific capture binding partners form second and third specific capture binding partner-anti-HCV antibody complexes with anti-HCV antibodies that are present in the test sample. Such second, third and fourth antigens may be one or more of at least one HCV antigen selected from the group consisting of core antigen, NS3, NS4, NS5, and portions thereof.

In addition immunoassays, besides includes at least one NS3h capture antigens, may include at least one anti-HCV capture antibody that will form a specific complex with a specific binding partner that is found in the test sample (i.e., an antigen or HCV protein that is found in the test sample) so as to form an anti-HCV antibody-third or fourth specific binding partner complex with the antigen that is present in the test sample. In certain embodiments, this specific binding pair is one that detects Core antigen in a test sample, and hence the binding pair is an anti-Core antibody for detection of the antigen (Core) in the test sample.

The order in which the test sample and the various specific binding partners are added to form the mixture may vary. In some embodiments, the first, second, third, etc. specific capture binding partners (i.e., antigens) and any anti-HCV capture antibody are immobilized on a solid phase. In still other embodiments, none of these components are immobilized but are instead all added at the same time to the test sample to effect capture onto the solid phase. The solid phase used in the immunoassay can be any solid phase known in the art, such as, but not limited to, a magnetic particle, a bead, a test tube, a microtiter plate, a cuvette, a membrane, a scaffolding molecule, a film, a filter paper, a disc and a chip.

After the immunocomplexes are formed between the specific capture binding partners and their respective anti-HCV antibodies found in the test sample, and any anti-HCV capture antibodies (e.g., anti-Core) and their respective HCV antigens or HCV proteins found in the test sample, any unbound anti-HCV antibody or HCV antigen/protein is removed from the complex using any technique known in the art. For example, the unbound anti-HCV antibody or antigen can be removed by washing. Desirably, however, the specific binding partners and any anti-HCV antibodies are present in excess of any anti-HCV antibody and antigens, respectively present in the test sample, such that all anti-HCV antibody and antigens that are present in the test sample become bound by the specific binding partner and any anti-HCV capture antibodies respectively.

After any unbound anti-HCV antibody and antigen is removed, detection is achieved by addition of a first specific detection binding partner (e.g., conjugate) to the mixture to form a first specific capture binding partner-anti-HCV antibody-first specific detection binding partner complex. The first specific detection binding partner may be a labeled antigen (e.g., NS3h antigen) or an anti-IgG antibody or an anti-IgM antibody. Moreover, the first specific detection binding partner may be labeled with or contain a detectable label as described above.

Any suitable detectable label as is known in the art can be used as any one or more of the detectable labels. For example, the detectable label can be a radioactive label (such as 3H, 125I, 35S, 14C, 32P, and 33P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

An exemplary acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another exemplary acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art. Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added. Upon the simultaneous or subsequent addition of at least one basic solution to the sample, a detectable signal, namely, a chemiluminescent signal, indicative of the presence of anti-HCV antibody (where capture is with an antigen) or antigen (where capture is with an antibody) is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of anti-HCV antibody and/or antigen in the sample can be quantified. Specifically, the amount of anti-HCV antibody and/or in the sample is proportional to the intensity of the signal generated. The amount of anti-HCV antibody and/or antigen present can be quantified by comparing the amount of light generated to a standard curve for anti-HCV antibody and/or antigen or by comparison to a reference standard. The standard curve can be generated using serial dilutions or solutions of known concentrations of anti-HCV antibody by mass spectroscopy, gravimetric methods, and other techniques known in the art.

Anti-HCV antibody and/or antigen immunoassays can be conducted using any suitable format known in the art. Generally speaking, in certain embodiments, a sample being tested for (for example, suspected of containing) anti-HCV antibodies can be contacted with a capture antigen and at least one detection conjugate peptide or conjugate antibody (which can be a second detection antibody or a third detection antibody), such as labeled anti-IgG and anti-IgM antibodies, either simultaneously or sequentially and in any order. Similarly, the test for presence of an antigen can be contacted with a captured antibody which binds the antigen in the test sample and the bound antigen may then be detected by a detection antibody.

For example, the test sample can be first contacted with at least two NS3h capture antigens and then (sequentially) with at least one detection antibody. Alternatively, the test sample can be first contacted with at least one detection antibody and then (sequentially) with at least two NS3h capture antigens. In yet another alternative, the test sample can be contacted simultaneously with a capture antigen and a detection antibody. In the sandwich assay format, a sample suspected of containing anti-HCV antibodies (or a fragment thereof) is first brought into contact with an at least two NS3h capture antigens under conditions that allow the formation of a first capture antigen/anti-HCV antibody complex and a second antigen/anti-HCV antibody complex. In certain assays, the same is repeated or simultaneously conducted with a second, third or more capture antigens. In a sandwich assay, the antigens) preferably, the at least two NS3h capture antigens are used in molar excess amounts of the maximum amount of anti-HCV antibodies expected in the test sample. For example, from about 5 ug to about 1 mg of antigen per mL of buffer (e.g., microparticle coating buffer) can be used.

Competitive inhibition immunoassays, which are often used to measure small analytes, comprise sequential and classic formats. In a sequential competitive inhibition immunoassay at least one or at least two NS3h capture antigens are coated onto a well of a microtiter plate. When the sample containing the antibody/antibodies of interest is added to the well, the antibody of interest binds to the capture antigens. After washing, a known amount of labeled (e.g., biotin or horseradish peroxidase (HRP)) antibody is added to the well. A substrate for an enzymatic label is necessary to generate a signal. An example of a suitable substrate for HRP is 3,3',5,5'-tetramethylbenzidine (TMB). After washing, the signal generated by the labeled antibody is measured and is inversely proportional to the amount of antibody in the sample. In a classic competitive inhibition immunoassay antigen for an antibody of interest is coated onto a well of a microtiter plate. However, unlike the sequential competitive inhibition immunoassay, the sample containing the antibody of interest (i.e., an anti-HCV antibody) and the labeled antibody are added to the well at the same. Any antibody in the sample competes with labeled antibody for binding to the capture antigen. After washing, the signal generated by the labeled analyte is measured and is inversely proportional to the amount of analyte in the sample.

In other embodiments, prior to contacting the test sample with the at least one or at least two NS3h capture antigens, the capture antigens can be bound to a solid support, which facilitates the separation of the first and second antigen/anti-HCV antibody complexes from the test sample. The substrate to which the capture antigens are bound can be any suitable solid support or solid phase that facilitates separation of the capture antigen-anti-HCV antibody complexes from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen to the substrate results; alternatively, a chemical coupling agent or other means can be used to bind covalently the antigen to the substrate, provided that such binding does not interfere with the ability of the antigen to bind to anti-HCV antibodies.

In other embodiments, the anti-HCV antibodies from the test sample can be bound with microparticles, which have been previously coated with antigen. If desired, one or more capture reagents, such as one or more or two or more NS3h antigens as described herein, each of which can be bound by an anti-HCV antibody, can be attached to solid phases in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828). If the capture reagents are attached to a mass spectrometry probe as the solid support, the amount of anti-HCV antibodies bound to the probe can be detected by laser desorption ionization mass spectrometry. Alternatively, a single column can be packed with different beads, which are derivatized with the one or more capture reagents, thereby capturing the anti-HCV antibody in a single place (see, antibody derivatized, bead-based technologies, e.g., the xMAP technology of Luminex (Austin, Tex.)).

In certain embodiments, after the test sample being assayed for anti-HCV antibodies is brought into contact with at least one or at least two NS3h antigens, the mixture is incubated in order to allow for the formation of a first and second antigen-anti-HCV antibody complexes. The incubation can be carried out, for example, at a pH of from about 4.5 to about 10.0, at a temperature of from about 2° C. to about 45° C., and for a period from at least about one (1)

minute to about eighteen (18) hours, or from about 1 to about 24 minutes, or for about 4 to about 18 minutes.

In certain embodiments, at least one detection antibody is employed and contains a detectable label. The detectable label can be bound to the at least one detection antibody prior to, simultaneously with, or after the formation of the (first or multiple) capture antigen/anti-HCV antibody/(second or multiple) detection antibody complex. Any detectable label known in the art can be used (see discussion above, including Polak and Van Noorden (1997) and Haugland (1996)). The detectable label can be bound to the antibodies (or antigens which may comprise detectable labels) either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The first and second (or more) capture antigen/anti-HCV antibody/labeled conjugate antigen complex can be, but does not have to be, separated from the remainder of the test sample prior to quantification of the label. For example, if the capture antigens are bound to a solid support, such as a well or a bead, separation can be accomplished by removing the fluid (of the test sample) from contact with the solid support. Alternatively, if the capture antigens are bound to a solid support, it can be simultaneously contacted with the anti-HCV antibody-containing sample and a labeled conjugate peptide to form a complex, followed by removal of the fluid (test sample) from contact with the solid support. If the capture antigens are not bound to a solid support, then complex does not have to be removed from the test sample for quantification of the amount of the label.

After formation of the detection complexes (e.g., capture antigen/subject antibody/labeled conjugate antigen), the amount of label in the complex may be quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of anti-HCV antibody or antigen in the test sample is determined, for example, by use of a standard curve that has been generated using serial dilutions of anti-HCV antibody or antigens of known concentration. Other than using serial dilutions of anti-HCV antibodies or HCV antigens, the standard curve can be generated gravimetrically, by mass spectroscopy and by other techniques known in the art.

In a chemiluminescent microparticle assay employing the ARCHITECT® analyzer, the conjugate diluent pH should generally be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 6.5+/−0.2. Solids preferably are less than about 0.2%, such as less than about 0.15%, less than about 0.14%, less than about 0.13%, less than about 0.12%, or less than about 0.11%, such as about 0.10%.

Commercially available anti-HCV antibodies as well as anti-IgG and anti-IgM antibodies can be used in the methods of assay and kits thereof. Commercially available antibodies include those available from Abnova (Walnut, Calif., and Taiwan) and GenWay Biotech, Inc. (San Diego, Calif.). See, also, European Pat. App. EP2099825 A2 regarding the preparation of anti-HCV antibodies. Any suitable control composition can be used in the anti-HCV antibody and HCV antigen immunoassays. The control composition generally comprises anti-HCV antibodies and known antigens and any desirable additives.

Generally, a predetermined level can be employed as a benchmark against which to assess results obtained upon assaying a test sample for anti-HCV antibodies. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., preeclampsia or cardiovascular disease) or with particular indicia can be made. Typically, the predetermined level is obtained with assays of reference subjects (or populations of subjects).

In particular, with respect to a predetermined level as employed for monitoring disease progression and/or treatment, the amount or concentration of anti-HCV antibodies may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for anti-HCV antibodies or HCV antigens is defined in accordance with standard practice. Because the levels of anti-HCV antibodies and/or HCV antigens in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable hepatitis, for example, and a "normal" (sometimes termed "control") patient or population is/are one(s) that exhibit(s) no detectable hepatitis, for example. Furthermore, given that anti-HCV antibodies and HCV antigens are not routinely found at a high level in the majority of the human population, a "normal subject" can be considered an individual with no substantial detectable increased or elevated amount or concentration of anti-HCV antibodies or HCV antigens, and a "normal" (sometimes termed "control") patient or population is/are one(s) that exhibit(s) no substantial detectable increased or elevated amount or concentration of anti-HCV antibodies. An "apparently normal subject" is one in which anti-HCV antibodies or HCV antigen has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, hepatitis, for example, as defined herein.

Accordingly, the methods described herein also can be used to determine whether or not a subject has or is at risk of developing hepatitis. Specifically, such a method can comprise the steps of: (a) determining the concentration or amount in a test sample from a subject of anti-HCV antibodies (e.g., using the methods described herein); and (b) comparing the concentration or amount of anti-HCV antibodies determined in step (a) with a predetermined level, wherein, if the concentration or amount of anti-HCV antibodies and/or HCV antigens determined in step (a) is favorable with respect to a predetermined level, then the subject is determined not to have or be at risk for hepatitis. However, if the concentration or amount of anti-HCV antibodies in step (a) is unfavorable with respect to the predetermined level, then the subject is determined to have or be at risk for hepatitis.

In certain embodiments, the methods described herein can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of anti-HCV antibodies (and optionally HCV antigens) is determined (e.g., using the at least one or at least two NS3h capture peptide methods described herein). After the concentration or amount of anti-HCV antibodies is determined, optionally the concentration or amount of anti-HCV antibodies is then compared with a predetermined level. If the concentration or amount of anti-HCV antibodies as determined in the first test sample is lower than the predetermined level, then the subject is not treated with one or more pharmaceutical compositions. However, if the concentration or amount of anti-HCV antibodies as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of anti-HCV antibodies (and optionally HCV antigens) is determined in the second or subsequent test sample is determined. The concentration or amount of anti-HCV antibodies and/or HCV antigens as determined in each of the second and subsequent test samples is then compared with the concentration or amount of anti-HCV antibodies and/or HCV antigens as determined in the first test sample (e.g., the test sample that was originally optionally compared to the predetermined level). If the concentration or amount of anti-HCV antibodies and/or HCV antigens as determined in step (c) is favorable when compared to the concentration or amount of anti-HCV antibodies and/or HCV antigens as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of anti-HCV antibodies and/or HCV antigens as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's anti-HCV antibodies and/or HCV antigens level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the assays described herein can be performed using a first test sample obtained from a subject where the first test sample is obtained from one source, such as urine, serum or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from hepatitis will benefit from treatment. In particular, the disclosure relates to HCV companion diagnostic methods and products. Thus, the method of "monitoring the treatment of disease in a subject" as described herein further optimally also can encompass selecting or identifying candidates for therapy. Thus, in particular embodiments, the disclosure also provides a method of determining whether a subject having, or at risk for, hepatitis is a candidate for therapy. Generally, the subject is one who has experienced some symptom of hepatitis or who has actually been diagnosed as having, or being at risk for, hepatitis and/or who demonstrates an unfavorable concentration or amount of anti-HCV antibodies or a fragment thereof and/or HCV antigens, as described herein.

The kits and systems (or components thereof), as well as the method of determining the concentration of anti-HCV antibodies and/or HCV antigens in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®. Some of the differences between an automated or semi-automated system as compared to a non-automated system (e.g., ELISA) include the substrate to which the first specific binding partner (e.g., antigen) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®). Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

EXAMPLES

Example 1

Single vs. Multiple NS3 Peptide HCV Assays for Varying HCV Antibody Titer Detection This Examples describes a comparison of varying HCV antibody titer detection between HCV assays that employ a single NS3 peptide (with various sizes and number of domains), and a combination HCV assay that employs both a full-length NS3 helicase peptide and a domain 1 only NS3 peptide. The results of this work are shown in Table 1 below.

TABLE 1

| Sample ID | ARCHITECT Anti-HCV (LN 6C37) S/CO | ARCHITECT Single Marker Assays | | | | | ARCHITECT HCV Ag/Ab Combo (NS3h + NS3h-D1 + Core Ab + Core Ag) S/CO |
|---|---|---|---|---|---|---|---|
| | | Core Ag S/CO | NS3 Ab (NS3h) S/CO | NS3 Ab (9NB49) S/CO | NS3 Ab (NS3h-D1) S/CO | Core Ab S/CO | |
| 11742342 | 3.99 | 0.06 | 2.79 | 0.06 | 0.07 | 0.18 | 2.28 |
| 11742158 | 9.57 | 0.04 | 19.36 | 0.11 | 0.11 | 0.24 | 16.34 |
| 11742354 | 15.06 | 0.06 | 0.72 | 11.40 | 73.48 | 0.13 | 62.75 |

In the 2nd column in Table 1 above, the ARCHITECT Anti-HCV assay was conducted as follows. In the first step, 10 uL human sample, 90 uL of assay specific diluent and 50 uL of microparticles coated with HCV NS3, core and NS4 antigens are added to a reaction vessel, vortexed, and incubated for 18 min. Following this incubation, the microparticles are sequestered at the side of the reaction vessel using a magnet while the reaction supernatant is removed. The microparticles are subsequently washed with water/detergent solution. During this first step HCV antigen-antibody complexes are formed and captured on the microparticles. In the second step, immediately following washing, 50 uL of reagent containing acridinylated anti-human IgG and IgM antibodies are added to the reaction vessel, vortexed and allowed to incubate for 4 minutes. During this step the acridinim:anti-human IgG and IgM conjugates further bind to the HCV antigen-antibody complexes formed in the 1st step. Following incubation, the microparticles are sequestered at the side of the reaction vessel using a magnet and the reaction supernatant removed. The microparticles are subsequently washed with water/detergent solution. Washed particles are suspended in a basic-hydrogen peroxide containing solution to activate the acridinium with simultaneous measurement of light output (in relative light units or RLU), which is proportional to the amount of conjugate bound onto the microparticles. The results are reported in Table 1 above, which shows progressively higher S/COs going from the top of the table down, corresponding to higher titers of antibody in the patient sample.

In the 3rd column in Table 2 above, the ARCHITECT Single Marker Core Ag assay was conducted as follows. In the first step, 110 uL human sample, 25 uL of assay specific diluent, 50 uL of reagent containing streptavidin coated microparticles, and 25 uL of reagent containing biotinylated anti-Core MAb (C11-7) are added to a reaction vessel, vortexed, and incubated for 18 min. During this first step, biotin:anti-core MAb:core Ag complexes are formed and captured on the microparticles. Following this incubation, the microparticles are sequestered at the side of the reaction vessel using a magnet while the reaction supernatant is removed. The microparticles are subsequently washed with water/detergent solution. In the second step, immediately following washing, 50 uL of reagent containing acridinylated anti-core MAbs (C11-9 and C11-14) is added to the reaction vessel, vortexed and allowed to incubate for 4 minutes. During this step the acridinim:anti-core MAb conjugate further binds to the biotin:anti-core MAb:core Ag complex formed in the 1st step. Following incubation, the microparticles are sequestered at the side of the reaction vessel using a magnet and the reaction supernatant removed. The microparticles are subsequently washed with water/detergent solution. Washed particles are suspended in a basic-hydrogen peroxide containing solution to activate the acridinium with simultaneous measurement of light output (in relative light units or RLU), which is proportional to the amount of conjugate bound onto the microparticles. The results are reported in Table 1 above, which shows there are no detectable levels of core Ag in these 3 samples.

In columns 4-7 in Table 1 above, the ARCHITECT Single Marker antibody assays were conducted as follows. In the first step, 110 uL human sample, 25 uL of reagent containing acridinylated HCV antigen (either NS3h-D1 (1192-1356), NS3h-DelN15 (1205-1658), 9NB49 (1192-1457) or core peptide (15-68, with a deletion at 34 and 48)), 50 uL of reagent containing streptavidin coated microparticles, and 25 uL of reagent containing biotinylated HCV antigens (either NS3h-D1 (1192-1356), NS3h-DelN15 (1205-1658), 9NB49 (1192-1457) or core peptide (15-68, with a deletion at 34 and 48)), are added to a reaction vessel, vortexed, and incubated for 18 min. During this first step biotin:antigen-HCV antibody-acridinium:antigen complexes are formed and captured on the microparticles. Following this incubation, the microparticles are sequestered at the side of the reaction vessel using a magnet while the reaction supernatant is removed. The microparticles are subsequently washed with water/detergent solution. In the second step, immediately following washing, 50 uL of reagent containing a wash solution is added to the reaction vessel, vortexed and allowed to incubate for 4 minutes. Following incubation, the microparticles are sequestered at the side of the reaction vessel using a magnet and the reaction supernatant removed. The microparticles are subsequently washed with water/detergent solution. Washed particles are suspended in a basic-hydrogen peroxide containing solution to activate the acridinium with simultaneous measurement of light output (in relative light units or RLU), which is proportional to the amount of conjugate bound onto the microparticles. The results are reported in Table 1 above, which shows the assay utilizing the NS3h-DelN15 (1205-1658) protein can detect the first 2 samples of lowest antibody titer while the assays using the NS3h-D1, 9NB49 and core peptide cannot. The last sample, of highest antibody titer, cannot be detected by the assay using the NS3h-DelN15 protein or the core peptide but can be detected by the assays using the 9NB49 and NS3h-D1 proteins. Furthermore the NS3h-D1 protein shows greater reactivity for this last sample than the 9NB49 protein.

In the last column in Table 1 above, the HCV Ag/Ab Combo assay was conducted. Importantly, this assay uses two different types of NS3 antigens, including one that contains all three of the helicase domains (e.g., for quantitatively or qualitatively (with a certain cut off) detecting low titer antibody samples), and one that contains only domain reagent containing acridinylated anti-core MAbs (C11-9 and C11-14) is added to the reaction vessel, vortexed and allowed to incubate for 4 minutes. During this step the acridinim:anti-HCV MAb conjugate further binds to the biotin:antigen-HCV antibody-acridinium:antigen complex formed in the 1st step. Following incubation, the microparticles are sequestered at the side of the reaction vessel using a magnet and the reaction supernatant removed. The microparticles are subsequently washed with water/detergent solution. Washed particles are suspended in a basic-hydrogen peroxide containing solution to activate the acridinium with simultaneous measurement of light output (in relative light units or RLU), which is proportional to the amount of conjugate bound onto the microparticles. The results are reported in Table 1 above, which shows that when the NS3h-DelN15 and NS3h-D1 proteins are combined into a combo assay all 3 samples are detected allowing for a larger range of sample antibody concentrations as compared to using a single NS3 protein alone.

In further work, a serial dilution series of 6 high titer HCV Ab positive samples were tested across two different 1-step anti-HCV NS3 assays that utilized 2 NS3 proteins. The NS3h assay, shown in table 2 below, utilized the NS3h-DelN15 (1205-1658) protein which has all three NS3 helicase domains. The NS3h-D1 assay, shown in table 2 below, used the NS3h-D1 (1192-1356) which encompasses only domain 1 of the NS3 helicase. The results of this testing are shown in Table 2 below.

TABLE 2

| | HCV Positive Sample Sample | Sample ID 11742271 | | Sample ID 11742348 | | Sample ID 11742256 | | Sample ID 11742200 | | Sample ID 11742353 | | Sample ID 11742193 | |
|---|---|---|---|---|---|---|---|---|---|---|---|---|---|
| Decreasing Ab Concentrations | Dilution Factor (1:x) in HCV Negative Plasma | NS3h Assay S/CO | NS3h-D1 Assay S/CO | NS3h Assay S/CO | NS3h-D1 Assay S/CO | NS3h Assay S/CO | NS3h-D1 Assay S/CO | NS3h Assay S/CO | NS3h-D1 Assay S/CO | NS3h Assay S/CO | NS3h-D1 Assay S/CO | NS3h Assay S/CO | NS3h-D1 Assay S/CO |
| ↓ | 1 | 0.07 | 36.28 | 0.12 | 42.00 | 0.14 | 45.63 | 0.06 | 28.23 | 0.06 | 21.10 | 0.08 | 27.33 |
| | 10 | 1.63 | 67.62 | 2.33 | 93.44 | 5.00 | 80.75 | 0.70 | 71.56 | 0.84 | 70.96 | 0.74 | 49.45 |
| | 100 | 61.92 | 37.90 | 30.20 | 63.75 | 98.57 | 22.91 | 21.50 | 78.88 | 29.82 | 86.80 | 19.18 | 49.31 |
| | 1000 | 128.06 | 3.52 | 125.89 | 6.20 | 85.23 | 1.87 | 112.93 | 9.65 | 134.69 | 12.20 | 124.80 | 6.96 |
| | 10000 | 30.07 | 0.29 | 47.76 | 0.44 | 13.46 | 0.15 | 29.29 | 0.95 | 43.59 | 1.05 | 45.87 | 0.59 |
| | 100000 | 3.16 | 0.04 | 5.66 | 0.05 | 1.35 | 0.03 | 2.56 | 0.11 | 4.34 | 0.11 | 5.04 | 0.07 |
| | 1000000 | 2.99 | 0.02 | 0.69 | 0.02 | 0.15 | 0.02 | 0.26 | 0.02 | 0.45 | 0.03 | 0.51 | 0.02 |

1 of the helicase (e.g., for quantitatively or qualitatively detecting high titer antibody samples). In the first step, 110 uL human sample, 25 uL of reagent containing acridinylated HCV NS3 antigens (both NS3h-D1 (1192-1356) and NS3h-DelN15 (1205-1658)) and a core antigen (15-68, with a deletion at 34 and 48), 50 uL of reagent containing streptavidin coated microparticles, and 25 uL of reagent containing biotinylated anti-Core MAb (C11-7), biotinylated HCV NS3 antigens (both NS3h-D1 (1192-1356) and NS3h-DelN15 (1205-1658)), and a biotinylated core antigen (15-68, with a deletion at 34 and 48), are added to a reaction vessel, vortexed, and incubated for 18 min. During this first step biotin:antigen-HCV antibody-acridinium:antigen complexes as well and biotin:anti-HCV MAb-HCV core Ag complexes are formed and captured on the microparticles. Following this incubation, the microparticles are sequestered at the side of the reaction vessel using a magnet while the reaction supernatant is removed. The microparticles are subsequently washed with water/detergent solution. In the second step, immediately following washing, 50 uL of As shown in Table 2, the 1-step assay composed of the single NS3 domain (D1) detected the higher concentrations of Ab but not the lower concentrations. The opposite is true for the assay composed of the full length NS3h protein that detects the lower antibody concentrations rather than the high antibody titers.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
    a) a first NS3h capture peptide that is no more than 200 amino acids in length and comprises the amino acid sequence of SEQ ID NO: 2 or SEQ ID NO: 3,
    b) a second NS3h capture peptide that is no more than 500 amino acids in length and comprises the amino acid sequence of SEQ ID NO: 5, SEQ ID NO: 7, or SEQ ID NO: 9, wherein each of the first and second NS3h capture peptides is able to bind to at least one subject antibody in a biological sample to form capture complexes,
    c) a first conjugate peptide that is no more than 200 amino acids in length and comprises the amino acid sequence of SEQ ID NO: 2 or SEQ ID NO: 3, and
    d) a second conjugate peptide that is no more than 500 amino acids in length and comprises the amino acid sequence of SEQ ID NO: 5, SEQ ID NO: 7, or SEQ ID NO: 9, wherein each of the first and second conjugate peptides (1) is able to bind to the at least one subject antibody in the capture complexes and (2) comprises a detectable label, and
    d) instructions for determining the presence of HCV in the biological sample.

2. The system of claim 1, wherein the at least one subject antibody is not present in the biological sample in purified form.

3. The system of claim 1, wherein the first NS3h capture peptide comprises the amino acid sequence of SEQ ID NO: 2.

4. The system of claim 1, wherein the first NS3h capture peptide comprises the amino acid sequence of SEQ ID NO: 3.

5. The system of claim 1, wherein the second NS3h capture peptide comprises the amino acid sequence of SEQ ID NO: 5.

6. The system of claim 1, wherein the second NS3h capture peptide comprises the amino acid sequence of SEQ ID NO: 7.

7. The system of claim 1, wherein the second NS3h capture peptide comprises the amino acid sequence of SEQ ID NO: 9.

8. The system of claim 1, wherein the first conjugate peptide comprises the amino acid sequence of SEQ ID NO: 2.

9. The system of claim 1, wherein the first conjugate peptide comprises the amino acid sequence of SEQ ID NO: 3.

10. The system of claim 1, wherein the second conjugate peptide comprises the amino acid sequence of SEQ ID NO: 5 and a detectable label.

11. The system of claim 1, wherein the second conjugate peptide comprises the amino acid sequence of SEQ ID NO: 7 and a detectable label.

12. The system of claim 1, wherein the second conjugate peptide comprises the amino acid sequence of SEQ ID NO: 9 and a detectable label.

13. A method of detecting hepatitis C virus (HCV) infection in a subject comprising:
    a) contacting a biological sample with the system of claim 1 to generate a mixed biological sample that comprises the biological sample, the first and second NS3h capture peptides, and the first and second conjugate peptides, wherein the biological sample is suspected of containing subject antibodies, and wherein the subject antibodies are not in purified form in the biological sample,
    b) incubating the mixed biological sample under conditions such that: (i) the first NS3h capture peptide specifically binds to at least one of the subject antibodies to form a first capture complex and the first conjugate peptide binds to the subject antibody in the first capture complex to form a first detectable complex, and (ii) the second NS3h capture peptide specifically binds to at least one of the subject antibodies to form a second capture complex and the second conjugate peptide binds to the subject antibody in the second capture complex to form a second detectable complex;
    c) washing the mixed biological sample to generate a washed sample; and
    d) detecting the presence of the first and/or second detectable complexes, thereby detecting the presence of past or present HCV infection in the subject, wherein the presence of both the first and second NS3h capture peptides in the mixed biological sample extends the dynamic range for qualitatively detecting the subject antibodies compared to only using the first or second NS3h capture peptide.

14. The method of claim 13, wherein the biological sample is suspected of containing HCV particles or fragments thereof and the method further comprises (e) contacting the sample with a first anti-HCV antibody to form a third complex comprising the first anti-HCV antibody bound to an HCV particle or fragment thereof, (f) contacting the biological sample with a detectably labeled second anti-HCV antibody that binds the HCV particle or fragment thereof in the third complex, and (g) detecting the third complex.

15. The method of claim 13, further comprising
    (a) contacting the biological sample with a first HCV core peptide, wherein the first HCV core peptide specifically binds to at least one of the subject antibodies in the biological sample to form a fourth complex; and (b) contacting the sample with a second HCV core peptide that is detectably labeled, wherein the second HCV core peptide binds to the subject antibody as part of the fourth complex.

16. The method of claim 13, wherein the subject is a human.

\* \* \* \* \*

SEQUENCE LISTING

<160> NUMBER OF SEQ ID NOS: 19

<210> SEQ ID NO 1
<211> LENGTH: 176
<212> TYPE: PRT
<213> ORGANISM: Artificial
<220> FEATURE:
<223> OTHER INFORMATION: Synthetic

<400> SEQUENCE: 1

Met Arg Ser Pro Val Phe Thr Asp Asn Ser Ser Pro Val Val Pro
1               5                   10                  15

Gln Ser Phe Gln Val Ala His Leu His Ala Pro Thr Gly Ser Gly Lys
            20                  25                  30

Ser Thr Lys Val Pro Ala Ala Tyr Ala Ala Gln Gly Tyr Lys Val Leu
        35                  40                  45

Val Leu Asn Pro Ser Val Ala Ala Thr Leu Gly Phe Gly Ala Tyr Met
    50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu
                85                  90                  95

Ala Asp Gly Gly Cys Ser Gly Gly Ala Tyr Asp Ile Ile Ile Cys Asp
            100                 105                 110

Glu Cys His Ser Thr Asp Ala Thr Ser Ile Leu Gly Ile Gly Thr Val
        115                 120                 125

Leu Asp Gln Ala Glu Thr Ala Gly Ala Arg Leu Val Val Leu Ala Thr
    130                 135                 140

Ala Thr Pro Pro Gly Ser Val Thr Gly Gly Gly Leu Asn Asp Ile Phe
145                 150                 155                 160

Glu Ala Gln Lys Ile Glu Trp His Gly His His His His His His
                165                 170                 175

<210> SEQ ID NO 2
<211> LENGTH: 177
<212> TYPE: PRT
<213> ORGANISM: Artificial
<220> FEATURE:
<223> OTHER INFORMATION: Synthetic

<400> SEQUENCE: 2

Met Ala Val Asp Phe Ile Pro Val Glu Asn Leu Glu Thr Thr Met Arg
1               5                   10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
        35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80

Ala His Gly Ile Asp Pro Asn Ile Arg Thr Gly Val Arg Thr Ile Thr
                85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

```
His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Gly Ser Gly Ser Gly His His His His
                165                 170                 175

His

<210> SEQ ID NO 3
<211> LENGTH: 194
<212> TYPE: PRT
<213> ORGANISM: Artificial
<220> FEATURE:
<223> OTHER INFORMATION: Synthetic

<400> SEQUENCE: 3

Met Ala Val Asp Phe Ile Pro Val Glu Asn Leu Glu Thr Thr Met Arg
1               5                   10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
            35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80

Ala His Gly Ile Asp Pro Asn Ile Arg Thr Gly Val Arg Thr Ile Thr
                85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Gly Ser Gly Ser Gly His His His His
                165                 170                 175

His Gly Gly Gly Leu Asn Asp Ile Phe Glu Ala Gln Lys Ile Glu Trp
            180                 185                 190

His Glu

<210> SEQ ID NO 4
<211> LENGTH: 1362
<212> TYPE: PRT
<213> ORGANISM: Artificial
<220> FEATURE:
<223> OTHER INFORMATION: Synthetic

<400> SEQUENCE: 4

Ala Thr Gly Cys Gly Thr Thr Cys Thr Cys Cys Gly Gly Thr Thr
1               5                   10                  15

Thr Cys Ala Cys Thr Gly Ala Cys Ala Ala Cys Thr Cys Thr Thr Cys
            20                  25                  30

Thr Cys Cys Gly Cys Cys Gly Gly Thr Thr Gly Thr Thr Cys Cys Gly
        35                  40                  45

Cys Ala Gly Thr Cys Thr Thr Thr Cys Cys Ala Gly Gly Thr Thr Gly
```

-continued

```
    50                  55                  60

Cys Thr Cys Ala Cys Cys Thr Gly Cys Ala Thr Gly Cys Thr Cys Cys
65                  70                  75                  80

Gly Ala Cys Thr Gly Gly Thr Thr Cys Thr Gly Gly Thr Ala Ala Ala
                85                  90                  95

Thr Cys Thr Ala Cys Thr Ala Ala Ala Gly Thr Thr Cys Cys Ala Gly
            100                 105                 110

Cys Thr Gly Cys Thr Thr Ala Cys Gly Cys Thr Gly Cys Thr Cys Ala
        115                 120                 125

Gly Gly Gly Thr Thr Ala Cys Ala Ala Ala Gly Thr Thr Cys Thr Gly
    130                 135                 140

Gly Thr Thr Cys Thr Gly Ala Ala Cys Cys Cys Gly Thr Cys Thr Gly
145                 150                 155                 160

Thr Thr Gly Cys Thr Gly Cys Thr Ala Cys Thr Cys Thr Gly Gly Gly
                165                 170                 175

Thr Thr Thr Cys Gly Gly Cys Gly Cys Cys Thr Ala Cys Ala Thr Gly
            180                 185                 190

Thr Cys Thr Ala Ala Ala Gly Cys Thr Cys Ala Cys Gly Gly Thr Ala
        195                 200                 205

Thr Cys Gly Ala Cys Cys Cys Gly Ala Ala Cys Ala Thr Thr Cys Gly
    210                 215                 220

Thr Ala Cys Thr Gly Gly Thr Gly Thr Ala Cys Gly Thr Ala Cys Thr
225                 230                 235                 240

Ala Thr Cys Ala Cys Thr Ala Cys Thr Gly Gly Thr Thr Cys Thr Cys
                245                 250                 255

Cys Gly Ala Thr Cys Ala Cys Thr Thr Ala Cys Thr Cys Thr Ala Cys
            260                 265                 270

Thr Thr Ala Cys Gly Gly Thr Ala Ala Ala Thr Thr Cys Cys Thr Gly
        275                 280                 285

Gly Cys Thr Gly Ala Cys Gly Gly Thr Gly Gly Thr Thr Gly Cys Thr
    290                 295                 300

Cys Thr Gly Gly Thr Gly Gly Thr Gly Cys Thr Thr Ala Cys Gly Ala
305                 310                 315                 320

Thr Ala Thr Cys Ala Thr Cys Ala Thr Cys Thr Gly Cys Gly Ala Cys
                325                 330                 335

Gly Ala Ala Thr Gly Cys Cys Ala Cys Thr Cys Thr Ala Cys Thr Gly
            340                 345                 350

Ala Cys Gly Cys Thr Ala Cys Thr Thr Cys Thr Ala Thr Cys Cys Thr
        355                 360                 365

Gly Gly Gly Thr Ala Thr Cys Gly Gly Thr Ala Cys Cys Gly Thr Thr
    370                 375                 380

Cys Thr Gly Gly Ala Cys Cys Ala Gly Gly Cys Thr Gly Ala Ala Ala
385                 390                 395                 400

Cys Thr Gly Cys Ala Gly Gly Thr Gly Cys Thr Cys Gly Thr Cys Thr
                405                 410                 415

Gly Gly Thr Thr Gly Thr Thr Cys Thr Gly Gly Cys Thr Ala Cys Thr
            420                 425                 430

Gly Cys Thr Ala Cys Thr Cys Cys Gly Cys Cys Gly Gly Gly Thr Thr
        435                 440                 445

Cys Thr Gly Thr Thr Ala Cys Thr Gly Thr Thr Cys Cys Gly Cys Ala
    450                 455                 460

Cys Cys Cys Gly Ala Ala Cys Ala Thr Cys Gly Ala Ala Gly Ala Ala
465                 470                 475                 480
```

-continued

```
Gly Thr Thr Gly Cys Thr Cys Thr Gly Thr Cys Gly Ala Cys Thr Ala
            485                 490                 495
Cys Thr Gly Gly Thr Gly Ala Ala Thr Cys Cys Gly Thr Thr
            500                 505                 510
Cys Thr Ala Cys Gly Gly Thr Ala Ala Gly Cys Thr Ala Thr Cys
            515                 520                 525
Cys Cys Gly Cys Thr Cys Gly Ala Gly Gly Thr Thr Ala Thr Cys Ala
    530                 535                 540
Ala Ala Gly Gly Thr Gly Gly Thr Cys Gly Thr Cys Ala Cys Cys Thr
545                 550                 555                 560
Gly Ala Thr Thr Thr Thr Cys Thr Gly Cys Cys Ala Cys Thr Cys Thr
                565                 570                 575
Ala Ala Ala Ala Ala Ala Ala Ala Thr Gly Cys Gly Ala Cys Gly
            580                 585                 590
Ala Ala Cys Thr Gly Gly Cys Thr Gly Cys Thr Ala Ala Gly Cys Thr
            595                 600                 605
Thr Gly Thr Thr Gly Cys Thr Cys Thr Gly Gly Thr Ala Thr Cys
            610                 615                 620
Ala Ala Cys Gly Cys Thr Gly Cys Thr Thr Gly Cys Thr Ala Cys Thr
625                 630                 635                 640
Ala Cys Cys Gly Thr Gly Thr Cys Thr Gly Gly Ala Cys Gly Thr
            645                 650                 655
Thr Thr Cys Thr Gly Thr Thr Ala Thr Cys Cys Gly Ala Cys Thr
            660                 665                 670
Thr Cys Thr Gly Gly Thr Gly Ala Cys Gly Thr Gly Thr Thr Gly
            675                 680                 685
Thr Thr Gly Thr Gly Gly Cys Cys Ala Cys Thr Gly Ala Cys Gly Cys
            690                 695                 700
Thr Cys Thr Gly Ala Thr Gly Ala Cys Thr Gly Gly Thr Thr Ala Cys
705                 710                 715                 720
Ala Cys Thr Gly Gly Thr Gly Ala Cys Thr Thr Cys Gly Ala Cys Thr
                725                 730                 735
Cys Thr Gly Thr Thr Ala Thr Cys Gly Ala Thr Gly Cys Ala Ala
            740                 745                 750
Cys Ala Cys Thr Thr Gly Cys Gly Thr Thr Ala Cys Thr Cys Ala Gly
            755                 760                 765
Ala Cys Cys Gly Thr Ala Gly Ala Thr Thr Thr Ala Gly Cys Cys
            770                 775                 780
Thr Gly Gly Ala Cys Cys Cys Gly Ala Cys Thr Thr Cys Ala Cys
785                 790                 795                 800
Thr Ala Thr Cys Gly Ala Ala Cys Gly Ala Thr Cys Ala Cys Cys
                805                 810                 815
Cys Thr Gly Cys Cys Gly Cys Ala Gly Gly Ala Thr Gly Cys Ala Gly
            820                 825                 830
Thr Thr Thr Cys Cys Gly Thr Ala Cys Cys Ala Gly Cys Gly
            835                 840                 845
Thr Cys Gly Thr Gly Gly Cys Cys Gly Thr Ala Cys Cys Gly Gly Thr
            850                 855                 860
Cys Gly Cys Gly Gly Cys Ala Ala Ala Cys Cys Gly Gly Gly Thr Ala
865                 870                 875                 880
Thr Thr Thr Ala Cys Cys Gly Thr Thr Thr Cys Gly Thr Gly Gly Cys
                885                 890                 895
```

Gly Cys Cys Gly Gly Cys Gly Ala Gly Cys Thr Cys Ala
            900                 905                 910

Thr Cys Cys Gly Gly Thr Ala Thr Gly Thr Thr Cys Gly Ala Thr Ala
            915                 920                 925

Gly Cys Thr Cys Thr Gly Thr Thr Cys Thr Gly Thr Gly Thr Gly Ala
            930                 935                 940

Gly Thr Gly Thr Thr Ala Thr Gly Ala Cys Gly Cys Gly Gly Gly Thr
945                 950                 955                 960

Thr Gly Cys Gly Cys Gly Thr Gly Gly Thr Ala Cys Gly Ala Ala Cys
            965                 970                 975

Thr Gly Ala Cys Thr Cys Cys Gly Gly Cys Thr Gly Ala Ala Ala Cys
            980                 985                 990

Thr Ala Cys Thr Gly Thr Ala Cys Gly Cys Cys Thr Gly Cys Gly Thr
            995                 1000                1005

Gly Cys Ala Thr Ala Cys Ala Thr Gly Ala Ala Thr Ala Cys Gly
            1010                1015                1020

Cys Cys Gly Gly Gly Thr Cys Thr Gly Cys Cys Gly Gly Thr Gly
            1025                1030                1035

Thr Gly Thr Cys Ala Ala Gly Ala Cys Cys Ala Cys Cys Thr Gly
            1040                1045                1050

Gly Ala Ala Thr Thr Thr Thr Gly Gly Gly Ala Ala Gly Gly Thr
            1055                1060                1065

Gly Thr Cys Thr Thr Thr Ala Cys Thr Gly Gly Cys Cys Thr Gly
            1070                1075                1080

Ala Cys Cys Cys Ala Thr Ala Thr Cys Gly Ala Cys Gly Cys Ala
            1085                1090                1095

Cys Ala Cys Thr Thr Thr Cys Thr Gly Thr Cys Cys Cys Ala Gly
            1100                1105                1110

Ala Cys Thr Ala Ala Ala Cys Ala Gly Thr Cys Thr Gly Gly Thr
            1115                1120                1125

Gly Ala Ala Ala Ala Cys Cys Thr Gly Cys Cys Gly Thr Ala Cys
            1130                1135                1140

Cys Thr Gly Gly Thr Gly Gly Cys Gly Thr Ala Thr Cys Ala Ala
            1145                1150                1155

Gly Cys Cys Ala Cys Thr Gly Thr Gly Thr Cys Gly Cys Cys Cys
            1160                1165                1170

Cys Gly Thr Gly Cys Gly Cys Ala Gly Cys Gly Gly Cys Cys Gly
            1175                1180                1185

Cys Cys Ala Cys Cys Gly Ala Gly Cys Thr Gly Gly Gly Ala Cys
            1190                1195                1200

Cys Ala Ala Ala Thr Gly Thr Gly Gly Ala Ala Gly Thr Gly Cys
            1205                1210                1215

Cys Thr Gly Ala Thr Cys Cys Gly Thr Cys Thr Gly Ala Ala Ala
            1220                1225                1230

Cys Cys Gly Ala Cys Cys Cys Thr Gly Cys Ala Cys Gly Gly Thr
            1235                1240                1245

Cys Cys Gly Ala Cys Gly Cys Ala Cys Thr Gly Cys Thr Gly Thr
            1250                1255                1260

Thr Ala Cys Cys Gly Cys Cys Thr Gly Gly Thr Gly Cys Gly Ala
            1265                1270                1275

Gly Thr Gly Cys Ala Gly Ala Ala Cys Gly Ala Ala Ala Thr Cys
            1280                1285                1290

Ala Cys Gly Cys Thr Gly Ala Cys Gly Cys Ala Cys Cys Cys Gly

```
              1295                1300                1305

Gly Thr Cys Ala Cys Thr Ala Ala Thr Ala Cys Ala Thr Thr
        1310                1315                1320

Ala Thr Gly Ala Cys Thr Thr Gly Cys Ala Thr Gly Ala Gly Cys
    1325                1330                1335

Gly Cys Ala Gly Ala Cys Cys Thr Gly Gly Ala Ala Gly Gly Thr
    1340                1345                1350

Gly Gly Cys Gly Gly Thr Cys Thr Gly
    1355                1360
```

<210> SEQ ID NO 5
<211> LENGTH: 450
<212> TYPE: PRT
<213> ORGANISM: Artificial
<220> FEATURE:
<223> OTHER INFORMATION: Synthetic

<400> SEQUENCE: 5

```
Met Arg Ser Pro Val Phe Thr Asp Asn Ser Pro Pro Val Val Pro
1               5                   10                  15

Gln Ser Phe Gln Val Ala His Leu His Ala Pro Thr Gly Ser Gly Lys
            20                  25                  30

Ser Thr Lys Val Pro Ala Ala Tyr Ala Ala Gln Gly Tyr Lys Val Leu
        35                  40                  45

Val Leu Asn Pro Ser Val Ala Ala Thr Leu Gly Phe Gly Ala Tyr Met
    50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu
                85                  90                  95

Ala Asp Gly Gly Cys Ser Gly Gly Ala Tyr Asp Ile Ile Cys Asp
                100                 105                 110

Glu Cys His Ser Thr Asp Ala Thr Ser Ile Leu Gly Ile Gly Thr Val
            115                 120                 125

Leu Asp Gln Ala Glu Thr Ala Gly Ala Arg Leu Val Val Leu Ala Thr
    130                 135                 140

Ala Thr Pro Pro Gly Ser Val Thr Val Pro His Pro Asn Ile Glu Glu
145                 150                 155                 160

Val Ala Leu Ser Thr Thr Gly Glu Ile Pro Phe Tyr Gly Lys Ala Ile
                165                 170                 175

Pro Leu Glu Val Ile Lys Gly Gly Arg His Leu Ile Phe Cys His Ser
            180                 185                 190

Lys Lys Lys Cys Asp Glu Leu Ala Ala Lys Leu Val Ala Leu Gly Ile
        195                 200                 205

Asn Ala Val Ala Tyr Tyr Arg Gly Leu Asp Val Ser Val Ile Pro Thr
    210                 215                 220

Ser Gly Asp Val Val Val Ala Thr Asp Ala Leu Met Thr Gly Tyr
225                 230                 235                 240

Thr Gly Asp Phe Asp Ser Val Ile Asp Cys Asn Thr Cys Val Thr Gln
                245                 250                 255

Thr Val Asp Phe Ser Leu Asp Pro Thr Phe Thr Ile Glu Thr Ile Thr
            260                 265                 270

Leu Pro Gln Asp Ala Val Ser Arg Thr Gln Arg Arg Gly Arg Thr Gly
        275                 280                 285

Arg Gly Lys Pro Gly Ile Tyr Arg Phe Val Ala Pro Gly Glu Arg Pro
```

```
                290             295             300
Ser Gly Met Phe Asp Ser Ser Val Leu Cys Glu Cys Tyr Asp Ala Gly
305                 310                 315                 320

Cys Ala Trp Tyr Glu Leu Thr Pro Ala Glu Thr Thr Val Arg Leu Arg
                325                 330                 335

Ala Tyr Met Asn Thr Pro Gly Leu Pro Val Cys Gln Asp His Leu Glu
                340                 345                 350

Phe Trp Glu Gly Val Phe Thr Gly Leu Thr His Ile Asp Ala His Phe
                355                 360                 365

Leu Ser Gln Thr Lys Gln Ser Gly Glu Asn Leu Pro Tyr Leu Val Ala
        370                 375                 380

Tyr Gln Ala Thr Val Cys Ala Arg Ala Gln Ala Pro Pro Ser Trp
385                 390                 395                 400

Asp Gln Met Trp Lys Cys Leu Ile Arg Leu Lys Pro Thr Leu His Gly
                405                 410                 415

Pro Thr Pro Leu Leu Tyr Arg Leu Gly Ala Val Gln Asn Glu Ile Thr
                420                 425                 430

Leu Thr His Pro Val Thr Lys Tyr Ile Met Thr Cys Met Ser Ala Asp
            435                 440                 445

Leu Glu
    450

<210> SEQ ID NO 6
<211> LENGTH: 1422
<212> TYPE: DNA
<213> ORGANISM: Artificial
<220> FEATURE:
<223> OTHER INFORMATION: Synthetic

<400> SEQUENCE: 6
atgcgttctc cggttttcac tgacaactct ctccgccgg ttgttccgca gtctttccag      60
gttgctcacc tgcatgctcc gactggttct ggtaaatcta ctaaagttcc agctgcttac     120
gctgctcagg ttacaaagt tctggttctg aacccgtctg ttgctgctac tctgggtttc      180
ggcgcctaca tgtctaaagc tcacggtatc gacccgaaca ttcgtactgg tgtacgtact     240
atcactactg ttctccgat cacttactct acttacggta aattcctggc tgacggtggt      300
tgctctggtg tgcttacga tatcatcatc tgcgacgaat gccactctac tgacgctact     360
tctatcctgg gtatcggtac cgttctggac caggctgaaa ctgcaggtgc tcgtctggtt     420
gttctggcta ctgctactcc gccgggttct gttactgttc gcacccgaa catcgaagaa     480 gttgctctgt cgactactgg tgaaatcccg ttctacggta agctatccc gctcgaggtt     540 atcaaaggtg tcgtcacct gatttttctgc cactctaaaa aaaatgcga cgaactggct     600 gctaagcttg ttgctctggg tatcaacgct gttgcttact accgtggtct ggacgtttct     660
gttatcccga cttctggtga cgttgttgtt gtggccactg acgctctgat gactggttac     720
actggtgact cgactctgt tatcgattgc aacacttgcg ttactcagac cgtagatttt     780
agcctggacc cgactttcac tatcgaaacg atcacccctgc cgcaggatgc agtttcccgt     840
acccagcgtc gtggccgtac cggtcgcggc aaacccgggta tttaccgttt cgtggcgccg     900
ggcgagcgtc catccggtat gttcgatagc tctgttctgt gtgagtgtta tgacgcgggt     960
tgcgcgtggt acgaactgac tccggctgaa actactgtac gcctgcgtgc atacatgaat    1020
acgccgggtc tgccggtgtg tcaagaccac ctggaatttt gggaaggtgt ctttactggc    1080
ctgacccata tcgacgcaca ctttctgtcc cagactaaac agtctggtga aaacctgccg    1140
```

```
tacctggtgg cgtatcaagc cactgtgtgc gcccgtgcgc aggcgccgcc accgagctgg    1200
gaccaaatgt ggaagtgcct gatccgtctg aaaccgaccc tgcacggtcc gacgccactg    1260
ctgtaccgcc tgggtgcagt gcagaacgaa atcacgctga cgcacccggt cactaaatac    1320
attatgactt gcatgagcgc agacctggaa ggtggcggtc tgaacgacat cttcgaggct    1380
cagaaaatcg aatggcacga aggtcatcat caccatcacc at                      1422
```

```
<210> SEQ ID NO 7
<211> LENGTH: 474
<212> TYPE: PRT
<213> ORGANISM: Artificial
<220> FEATURE:
<223> OTHER INFORMATION: Synthetic

<400> SEQUENCE: 7

Met Arg Ser Pro Val Phe Thr Asp Asn Ser Pro Val Val Pro
1               5                   10                  15

Gln Ser Phe Gln Val Ala His Leu His Ala Pro Thr Gly Ser Gly Lys
            20                  25                  30

Ser Thr Lys Val Pro Ala Ala Tyr Ala Ala Gln Gly Tyr Lys Val Leu
        35                  40                  45

Val Leu Asn Pro Ser Val Ala Ala Thr Leu Gly Phe Gly Ala Tyr Met
    50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu
                85                  90                  95

Ala Asp Gly Gly Cys Ser Gly Gly Ala Tyr Asp Ile Ile Ile Cys Asp
            100                 105                 110

Glu Cys His Ser Thr Asp Ala Thr Ser Ile Leu Gly Ile Gly Thr Val
        115                 120                 125

Leu Asp Gln Ala Glu Thr Ala Gly Ala Arg Leu Val Val Leu Ala Thr
    130                 135                 140

Ala Thr Pro Pro Gly Ser Val Thr Val Pro His Pro Asn Ile Glu Glu
145                 150                 155                 160

Val Ala Leu Ser Thr Thr Gly Glu Ile Pro Phe Tyr Gly Lys Ala Ile
                165                 170                 175

Pro Leu Glu Val Ile Lys Gly Gly Arg His Leu Ile Phe Cys His Ser
            180                 185                 190

Lys Lys Lys Cys Asp Glu Leu Ala Ala Lys Leu Val Ala Leu Gly Ile
        195                 200                 205

Asn Ala Val Ala Tyr Tyr Arg Gly Leu Asp Val Ser Val Ile Pro Thr
    210                 215                 220

Ser Gly Asp Val Val Val Ala Thr Asp Ala Leu Met Thr Gly Tyr
225                 230                 235                 240

Thr Gly Asp Phe Asp Ser Val Ile Asp Cys Asn Thr Cys Val Thr Gln
                245                 250                 255

Thr Val Asp Phe Ser Leu Asp Pro Thr Phe Thr Ile Glu Thr Ile Thr
            260                 265                 270

Leu Pro Gln Asp Ala Val Ser Arg Thr Gln Arg Arg Gly Arg Thr Gly
        275                 280                 285

Arg Gly Lys Pro Gly Ile Tyr Arg Phe Val Ala Pro Gly Glu Arg Pro
    290                 295                 300

Ser Gly Met Phe Asp Ser Ser Val Leu Cys Glu Cys Tyr Asp Ala Gly
```

```
                305                 310                 315                 320
Cys Ala Trp Tyr Glu Leu Thr Pro Ala Glu Thr Thr Val Arg Leu Arg
                    325                 330                 335

Ala Tyr Met Asn Thr Pro Gly Leu Pro Val Cys Gln Asp His Leu Glu
                    340                 345                 350

Phe Trp Glu Gly Val Phe Thr Gly Leu Thr His Ile Asp Ala His Phe
                    355                 360                 365

Leu Ser Gln Thr Lys Gln Ser Gly Glu Asn Leu Pro Tyr Leu Val Ala
    370                 375                 380

Tyr Gln Ala Thr Val Cys Ala Arg Ala Gln Ala Pro Pro Ser Trp
385                 390                 395                 400

Asp Gln Met Trp Lys Cys Leu Ile Arg Leu Lys Pro Thr Leu His Gly
                    405                 410                 415

Pro Thr Pro Leu Leu Tyr Arg Leu Gly Ala Val Gln Asn Glu Ile Thr
                    420                 425                 430

Leu Thr His Pro Val Thr Lys Tyr Ile Met Thr Cys Met Ser Ala Asp
                    435                 440                 445

Leu Glu Gly Gly Gly Leu Asn Asp Ile Phe Glu Ala Gln Lys Ile Glu
    450                 455                 460

Trp His Glu Gly His His His His His His
465                 470
```

<210> SEQ ID NO 8
<211> LENGTH: 1434
<212> TYPE: DNA
<213> ORGANISM: Artificial
<220> FEATURE:
<223> OTHER INFORMATION: Synthetic

<400> SEQUENCE: 8

```
atgcgttctc cggttttcac tgacaactct ctctccgccgg ttgttccgca gtctttccag      60
gttgctcacc tgcatgctcc gactggttct ggtaaatcta ctaaagttcc agctgcttac     120
gctgctcagg ttacaaagt tctggttctg aacccgtctg ttgctgctac tctgggtttc     180
ggcgcctaca tgtctaaagc tcacggtatc gacccgaaca ttcgtactgg tgtacgtact     240
atcactactg gttctccgat cacttactct acttacggta aattcctggc tgacggtggt     300
tgctctggtg tgcttacga tatcatcatc tgcgacgaat gccactctac tgacgctact     360
tctatcctgg gtatcggtac cgttctggac caggctgaaa ctgcaggtgc tcgtctggtt     420
gttctggcta ctgctactcc gccgggttct gttactgttc cgcacccgaa catcgaagaa     480
gttgctctgt cgactactgg tgaaatcccg ttctacggta agctatccc gctcgaggtt     540
atcaaaggtg tcgtcacct gattttctgc cactctaaaa aaaatgcga cgaactggct     600
gctaagcttg ttgctctggg tatcaacgct gttgcttact accgtggtct ggacgtttct     660
gttatcccga cttctggtga cgttgttgtt gtggccactg acgctctgat gactggttac     720
actggtgact tcgactctgt tatcgattgc aacacttgcg ttactcagac cgtagatttt     780
agcctggacc cgactttcac tatcgaaacg atcaccctgc cgcaggatgc agtttcccgt     840
acccagcgtc gtggccgtac cggtcgcggc aaaccgggta tttaccgttt cgtggcgccg     900
ggcgagcgtc catccggtat gttcgatagc tctgttctgt gtgagtgtta tgacgcgggt     960
tgcgcgtggt acgaactgac tccggctgaa actactgtac gcctgcgtgc atacatgaat    1020
acgccgggtc tgccggtgtg tcaagaccac ctggaatttt gggaaggtgt ctttactggc    1080
ctgacccata tcgacgcaca ctttctgtcc cagactaaac agtctggtga aaacctgccg    1140
```

```
tacctggtgg cgtatcaagc cactgtgtgc gcccgtgcgc aggcgccgcc accgagctgg   1200
gaccaaatgt ggaagtgcct gatccgtctg aaaccgaccc tgcacggtcc gacgccactg   1260
ctgtaccgcc ttggtgcagt gcagaacgaa atcacgctga cccatccggt cactaaatac   1320
attatgactt gcatgagcgc agacctggaa acaacaacaa caataacaa taacaacaac   1380 gatgaatgtc atgccgcgga tagaggcggc tgcggtcatc atcaccatca ccat   1434
```

<210> SEQ ID NO 9
<211> LENGTH: 478
<212> TYPE: PRT
<213> ORGANISM: Artificial
<220> FEATURE:
<223> OTHER INFORMATION: Synthetic

<400> SEQUENCE: 9

```
Met Arg Ser Pro Val Phe Thr Asp Asn Ser Pro Val Val Pro
1               5                   10                  15

Gln Ser Phe Gln Val Ala His Leu His Ala Pro Thr Gly Ser Gly Lys
            20                  25                  30

Ser Thr Lys Val Pro Ala Ala Tyr Ala Ala Gln Gly Tyr Lys Val Leu
        35                  40                  45

Val Leu Asn Pro Ser Val Ala Ala Thr Leu Gly Phe Gly Ala Tyr Met
    50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu
                85                  90                  95

Ala Asp Gly Gly Cys Ser Gly Gly Ala Tyr Asp Ile Ile Ile Cys Asp
            100                 105                 110

Glu Cys His Ser Thr Asp Ala Thr Ser Ile Leu Gly Ile Gly Thr Val
        115                 120                 125

Leu Asp Gln Ala Glu Thr Ala Gly Ala Arg Leu Val Val Leu Ala Thr
    130                 135                 140

Ala Thr Pro Pro Gly Ser Val Thr Val Pro His Pro Asn Ile Glu Glu
145                 150                 155                 160

Val Ala Leu Ser Thr Thr Gly Glu Ile Pro Phe Tyr Gly Lys Ala Ile
                165                 170                 175

Pro Leu Glu Val Ile Lys Gly Gly Arg His Leu Ile Phe Cys His Ser
            180                 185                 190

Lys Lys Lys Cys Asp Glu Leu Ala Ala Lys Leu Val Ala Leu Gly Ile
        195                 200                 205

Asn Ala Val Ala Tyr Tyr Arg Gly Leu Asp Val Ser Val Ile Pro Thr
    210                 215                 220

Ser Gly Asp Val Val Val Ala Thr Asp Ala Leu Met Thr Gly Tyr
225                 230                 235                 240

Thr Gly Asp Phe Asp Ser Val Ile Asp Cys Asn Thr Cys Val Thr Gln
                245                 250                 255

Thr Val Asp Phe Ser Leu Asp Pro Thr Phe Thr Ile Glu Thr Ile Thr
            260                 265                 270

Leu Pro Gln Asp Ala Val Ser Arg Thr Gln Arg Arg Gly Arg Thr Gly
        275                 280                 285

Arg Gly Lys Pro Gly Ile Tyr Arg Phe Val Ala Pro Gly Glu Arg Pro
    290                 295                 300

Ser Gly Met Phe Asp Ser Ser Val Leu Cys Glu Cys Tyr Asp Ala Gly
```

```
                    305                 310                 315                 320
Cys Ala Trp Tyr Glu Leu Thr Pro Ala Glu Thr Thr Val Arg Leu Arg
                325                 330                 335

Ala Tyr Met Asn Thr Pro Gly Leu Pro Val Cys Gln Asp His Leu Glu
                340                 345                 350

Phe Trp Glu Gly Val Phe Thr Gly Leu Thr His Ile Asp Ala His Phe
                355                 360                 365

Leu Ser Gln Thr Lys Gln Ser Gly Glu Asn Leu Pro Tyr Leu Val Ala
            370                 375                 380

Tyr Gln Ala Thr Val Cys Ala Arg Ala Gln Ala Pro Pro Pro Ser Trp
385                 390                 395                 400

Asp Gln Met Trp Lys Cys Leu Ile Arg Leu Lys Pro Thr Leu His Gly
                405                 410                 415

Pro Thr Pro Leu Leu Tyr Arg Leu Gly Ala Val Gln Asn Glu Ile Thr
                420                 425                 430

Leu Thr His Pro Val Thr Lys Tyr Ile Met Thr Cys Met Ser Ala Asp
            435                 440                 445

Leu Glu Asn Asn Asn Asn Asn Asn Asn Asn Asn Asp Glu Cys His
        450                 455                 460

Ala Ala Asp Arg Gly Gly Cys Gly His His His His His
465                 470                 475

<210> SEQ ID NO 10
<211> LENGTH: 1287
<212> TYPE: DNA
<213> ORGANISM: Artificial
<220> FEATURE:
<223> OTHER INFORMATION: Synthetic

<400> SEQUENCE: 10
atggctgttg actttatccc ggttgaaaat ctcgagacta ctatgcgttc tccggttttc      60
actgacaact cttctccgcc ggttgttccg cagtcttttc caggttgctca cctgcatgct    120 ccgactggtt ctggtaaatc tactaaagtt ccagctgctt acgctgctca gggttacaaa    180
gttctggttc tgaacccgtc tgttgctgct actctgggtt cggcgcccta catgtctaaa    240
gctcacggta tcgacccgaa cattcgtact ggtgtacgta ctatcactac tggttctccg    300
atcacttact ctacttacgg taaattcctg gctgacggtg ttgctctgg tggtgcttac     360 gatatcatca tctgcgacga atgccactct actgacgcta cttctatcct gggtatcggt    420
accgttctgg accaggctga aactgcaggt gctcgtctgg ttgttctggc tactgctact    480
ccgccgggtt ctgttactgt tccgcacccg aacatcgaag aagttgctct gtcgactact    540
ggtgaaatcc cgttctacgg taagctatc ccgctcgagg ttatcaaagg tggtcgtcac     600
ctgattttct gccactctaa aaaaaaatgc gacgaactgg ctgctaagct tgttgctctg    660
ggtatcaacg ctgttgctta ctaccgtggt ctggacgttt ctgttatccc gacttctggt    720
gacgttgttg ttgtggccac tgacgctctg atgactggta cactggtga cttcgactct     780 gttatcgatt gcaacacttg caattccatg tctaccaacc cgaaaccgca gaaaaaaaac    840
aaacgtaaca ccaaccgtcg tccgcaggac gttaaattcc cggtggtgg tcagatcgtt     900 ggtggtgttt acctgctgcc gcgtcgtggt ccgcgtctgg tgttcgtgc tacgcgtaaa     960 acctctgaac gttctcagcc gcgtgggcgt cgtcagccga tcccgaaagc tcgtcgtccg   1020
gaaggtcgta cctgggctca gccggggtac cgtggccgc tgtacggtaa cgaaggttgc   1080
ggttgggctg ttggctgct gtctccgcgt ggatctcgtc cgtcttgggg tccgaccgac    1140
```

```
ccgcgtcgtc gttctcgtaa ccttggtaaa gttatcgata ccctgacctg cggtttcgct    1200
gacctgatgg gttacatacc gctggttgga gctccgctgg gtggtgctgc tcgtgctggt    1260
tctggcagcc atcatcacca tcaccat                                        1287
```

<210> SEQ ID NO 11
<211> LENGTH: 429
<212> TYPE: PRT
<213> ORGANISM: Artificial
<220> FEATURE:
<223> OTHER INFORMATION: Synthetic

<400> SEQUENCE: 11

```
Met Ala Val Asp Phe Ile Pro Val Glu Asn Leu Glu Thr Thr Met Arg
1               5                   10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
        35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80

Ala His Gly Ile Asp Pro Asn Ile Arg Thr Gly Val Arg Thr Ile Thr
                85                  90                  95

Thr Gly Ser Pro Ile Thr Tyr Ser Thr Tyr Gly Lys Phe Leu Ala Asp
            100                 105                 110

Gly Gly Cys Ser Gly Gly Ala Tyr Asp Ile Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
    210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255

Asp Phe Asp Ser Val Ile Asp Cys Asn Thr Cys Asn Ser Met Ser Thr
            260                 265                 270

Asn Pro Lys Pro Gln Lys Lys Asn Lys Arg Asn Thr Asn Arg Arg Pro
        275                 280                 285

Gln Asp Val Lys Phe Pro Gly Gly Gly Gln Ile Val Gly Gly Val Tyr
    290                 295                 300

Leu Leu Pro Arg Arg Gly Pro Arg Leu Gly Val Arg Ala Thr Arg Lys
305                 310                 315                 320

Thr Ser Glu Arg Ser Gln Pro Arg Gly Arg Gln Pro Ile Pro Lys
                325                 330                 335
```

```
Ala Arg Arg Pro Glu Gly Arg Thr Trp Ala Gln Pro Gly Tyr Pro Trp
            340                 345                 350

Pro Leu Tyr Gly Asn Glu Gly Cys Gly Trp Ala Gly Trp Leu Leu Ser
            355                 360                 365

Pro Arg Gly Ser Arg Pro Ser Trp Gly Pro Thr Asp Pro Arg Arg
            370                 375                 380

Ser Arg Asn Leu Gly Lys Val Ile Asp Thr Leu Thr Cys Gly Phe Ala
385                 390                 395                 400

Asp Leu Met Gly Tyr Ile Pro Leu Val Gly Ala Pro Leu Gly Ala
                405                 410                 415

Ala Arg Ala Gly Ser Gly Ser His His His His His His
            420                 425

<210> SEQ ID NO 12
<211> LENGTH: 52
<212> TYPE: PRT
<213> ORGANISM: Artificial
<220> FEATURE:
<223> OTHER INFORMATION: Synthetic

<400> SEQUENCE: 12

Thr Asn Arg Arg Pro Gln Asp Val Lys Phe Pro Gly Gly Gly Gln Ile
1               5                   10                  15

Val Gly Gly Tyr Leu Leu Pro Arg Arg Gly Pro Arg Leu Gly Val Arg
            20                  25                  30

Thr Arg Lys Thr Ser Glu Arg Ser Gln Pro Arg Gly Arg Arg Gln Pro
            35                  40                  45

Ile Pro Lys Ala
    50

<210> SEQ ID NO 13
<211> LENGTH: 180
<212> TYPE: PRT
<213> ORGANISM: Artificial
<220> FEATURE:
<223> OTHER INFORMATION: Synthetic

<400> SEQUENCE: 13

Met Arg Ser Pro Val Phe Thr Asp Asn Ser Ser Pro Pro Val Val Pro
1               5                   10                  15

Gln Ser Phe Gln Val Ala His Leu His Ala Pro Thr Gly Ser Gly Lys
            20                  25                  30

Ser Thr Lys Val Pro Ala Ala Tyr Ala Ala Gln Gly Tyr Lys Val Leu
            35                  40                  45

Val Leu Asn Pro Ser Val Ala Ala Thr Leu Gly Phe Gly Ala Tyr Met
        50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu
                85                  90                  95

Ala Asp Gly Gly Cys Ser Gly Gly Ala Tyr Asp Ile Ile Ile Cys Asp
            100                 105                 110

Glu Cys His Ser Thr Asp Ala Thr Ser Ile Leu Gly Ile Gly Thr Val
            115                 120                 125

Leu Asp Gln Ala Glu Thr Ala Gly Ala Arg Leu Val Val Leu Ala Thr
        130                 135                 140

Ala Thr Pro Pro Gly Ser Val Thr Asn Asn Asn Asn Asn Asn Asn Asn
```

```
145                 150                 155                 160
Asn Asn Asp Glu Cys His Ala Ala Asp Arg Gly Gly Cys Gly His His
                165                 170                 175
His His His His
            180

<210> SEQ ID NO 14
<211> LENGTH: 162
<212> TYPE: PRT
<213> ORGANISM: Artificial
<220> FEATURE:
<223> OTHER INFORMATION: Synthetic

<400> SEQUENCE: 14

Met Arg Ser Pro Val Phe Thr Asp Asn Ser Pro Pro Val Val Pro
1               5                  10                  15

Gln Ser Phe Gln Val Ala His Leu His Ala Pro Thr Gly Ser Gly Lys
                20                  25                  30

Ser Thr Lys Val Pro Ala Ala Tyr Ala Ala Gln Gly Tyr Lys Val Leu
            35                  40                  45

Val Leu Asn Pro Ser Val Ala Ala Thr Leu Gly Phe Gly Ala Tyr Met
50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu
                85                  90                  95

Ala Asp Gly Gly Cys Ser Gly Gly Ala Tyr Asp Ile Ile Ile Cys Asp
            100                 105                 110

Glu Cys His Ser Thr Asp Ala Thr Ser Ile Leu Gly Ile Gly Thr Val
            115                 120                 125

Leu Asp Gln Ala Glu Thr Ala Gly Ala Arg Leu Val Val Leu Ala Thr
        130                 135                 140

Ala Thr Pro Pro Gly Ser Val Thr Gly Ser Gly Ser Gly His His His
145                 150                 155                 160

His His

<210> SEQ ID NO 15
<211> LENGTH: 798
<212> TYPE: DNA
<213> ORGANISM: Artificial
<220> FEATURE:
<223> OTHER INFORMATION: Synthetic

<400> SEQUENCE: 15
gctgttgact ttatcccggt tgaaaatctc gagactacta tgcgttctcc ggttttcact      60
gacaactctt ctccgccggt tgttccgcag tctttccagg ttgctcacct gcatgctccg     120
actggttctg gtaaatctac taaagttcca gctgcttacg ctgctcaggg ttacaaagtt     180
ctggttctga acccgtctgt tgctgctact ctgggtttcg gcgcctacat gtctaaagct     240
cacggtatcg acccgaacat tcgtactggt gtacgtacta tcactactgg ttctccgatc     300
acttactcta cttacggtaa attcctggct gacggtggtt gctctggtgg tgcttacgat     360
atcatcatct gcgacgaatg ccactctact gacgctactt ctatcctggg tatcggtacc     420
gttctggacc aggctgaaac tgcaggtgct cgtctggttg ttctggctac tgctactccg     480
ccgggttctg ttactgttcc gcacccgaac atcgaagaag ttgctctgtc gactactggt     540
gaaatcccgt tctacggtaa agctatcccg ctcgaggtta tcaaaggtgg tcgtcacctg     600
```

-continued

```
attttctgcc actctaaaaa aaaatgcgac gaactggctg ctaagcttgt tgctctgggt    660
atcaacgctg ttgcttacta ccgtggtctg gacgtttctg ttatcccgac ttctggtgac    720
gttgttgttg tggccactga cgctctgatg actggttaca ctggtgactt cgactctgtt    780
atcgattgca acacttgc                                                  798
```

<210> SEQ ID NO 16
<211> LENGTH: 266
<212> TYPE: PRT
<213> ORGANISM: Artificial
<220> FEATURE:
<223> OTHER INFORMATION: Synthetic

<400> SEQUENCE: 16

```
Ala Val Asp Phe Ile Pro Val Glu Asn Leu Glu Thr Thr Met Arg Ser
1               5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
        35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
        115                 120                 125

Ser Thr Asp Ala Thr Ser Ile Leu Gly Ile Gly Thr Val Leu Asp Gln
    130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
        195                 200                 205

Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265
```

<210> SEQ ID NO 17
<211> LENGTH: 38
<212> TYPE: PRT
<213> ORGANISM: Artificial
<220> FEATURE:
<223> OTHER INFORMATION: Synthetic

<400> SEQUENCE: 17

Met Gly Tyr Ile Pro Leu Val Gly Ala Pro Leu Gly Gly Ala Ala Arg
1               5                   10                  15

Ala Leu Ala His Gly Val Arg Val Leu Glu Asp Gly Val Asn Tyr Ala
                20                  25                  30

Thr Gly Asn Leu Pro Gly
            35

<210> SEQ ID NO 18
<211> LENGTH: 600
<212> TYPE: PRT
<213> ORGANISM: Hepatitis C virus

<400> SEQUENCE: 18

Tyr Thr Asn Val Asp Gln Asp Leu Val Gly Trp Pro Ala Pro Gln Gly
1               5                   10                  15

Ser Arg Ser Leu Thr Pro Cys Thr Cys Gly Ser Ser Asp Leu Tyr Leu
                20                  25                  30

Val Thr Arg His Ala Asp Val Ile Pro Val Arg Arg Arg Gly Asp Ser
                35                  40                  45

Arg Gly Ser Leu Leu Ser Pro Arg Pro Ile Ser Tyr Leu Lys Gly Ser
    50                  55                  60

Ser Gly Gly Pro Leu Leu Cys Pro Ala Gly His Ala Val Gly Ile Phe
65                  70                  75                  80

Arg Ala Ala Val Cys Thr Arg Gly Val Ala Lys Ala Val Asp Phe Ile
                85                  90                  95

Pro Val Glu Asn Leu Glu Thr Thr Met Arg Ser Pro Val Phe Thr Asp
            100                 105                 110

Asn Ser Ser Pro Pro Val Val Pro Gln Ser Phe Gln Val Ala His Leu
        115                 120                 125

His Ala Pro Thr Gly Ser Gly Lys Ser Thr Lys Val Pro Ala Ala Tyr
    130                 135                 140

Ala Ala Gln Gly Tyr Lys Val Leu Val Leu Asn Pro Ser Val Ala Ala
145                 150                 155                 160

Thr Leu Gly Phe Gly Ala Tyr Met Ser Lys Ala His Gly Ile Asp Pro
                165                 170                 175

Asn Ile Arg Thr Gly Val Arg Thr Ile Thr Thr Gly Ser Pro Ile Thr
            180                 185                 190

Tyr Ser Thr Tyr Gly Lys Phe Leu Ala Asp Gly Gly Cys Ser Gly Gly
        195                 200                 205

Ala Tyr Asp Ile Ile Ile Cys Asp Glu Cys His Ser Thr Asp Ala Thr
    210                 215                 220

Ser Ile Leu Gly Ile Gly Thr Val Leu Asp Gln Ala Glu Thr Ala Gly
225                 230                 235                 240

Ala Arg Leu Val Val Leu Ala Thr Ala Thr Pro Pro Gly Ser Val Thr
                245                 250                 255

Val Pro His Pro Asn Ile Glu Glu Val Ala Leu Ser Thr Thr Gly Glu
            260                 265                 270

Ile Pro Phe Tyr Gly Lys Ala Ile Pro Leu Glu Val Ile Lys Gly Gly
        275                 280                 285

Arg His Leu Ile Phe Cys His Ser Lys Lys Cys Asp Glu Leu Ala
    290                 295                 300

Ala Lys Leu Val Ala Leu Gly Ile Asn Ala Val Ala Tyr Tyr Arg Gly
305                 310                 315                 320

Leu Asp Val Ser Val Ile Pro Thr Ser Gly Asp Val Val Val Val Ala

|   |   |   | 325 |   |   | 330 |   |   |   | 335 |   |
|---|---|---|---|---|---|---|---|---|---|---|---|

Thr Asp Ala Leu Met Thr Gly Tyr Thr Gly Asp Phe Asp Ser Val Ile
            340                 345                 350

Asp Cys Asn Thr Cys Val Thr Gln Thr Val Asp Phe Ser Leu Asp Pro
            355                 360                 365

Thr Phe Thr Ile Glu Thr Ile Thr Leu Pro Gln Asp Ala Val Ser Arg
            370                 375                 380

Thr Gln Arg Arg Gly Arg Thr Gly Arg Gly Lys Pro Gly Ile Tyr Arg
385                 390                 395                 400

Phe Val Ala Pro Gly Glu Arg Pro Ser Gly Met Phe Asp Ser Ser Val
                405                 410                 415

Leu Cys Glu Cys Tyr Asp Ala Gly Cys Ala Trp Tyr Glu Leu Thr Pro
                420                 425                 430

Ala Glu Thr Thr Val Arg Leu Arg Ala Tyr Met Asn Thr Pro Gly Leu
            435                 440                 445

Pro Val Cys Gln Asp His Leu Glu Phe Trp Glu Gly Val Phe Thr Gly
            450                 455                 460

Leu Thr His Ile Asp Ala His Phe Leu Ser Gln Thr Lys Gln Ser Gly
465                 470                 475                 480

Glu Asn Leu Pro Tyr Leu Val Ala Tyr Gln Ala Thr Val Cys Ala Arg
                485                 490                 495

Ala Gln Ala Pro Pro Ser Trp Asp Gln Met Trp Lys Cys Leu Ile
            500                 505                 510

Arg Leu Lys Pro Thr Leu His Gly Pro Thr Pro Leu Leu Tyr Arg Leu
            515                 520                 525

Gly Ala Val Gln Asn Glu Ile Thr Leu Thr His Pro Val Thr Lys Tyr
            530                 535                 540

Ile Met Thr Cys Met Ser Ala Asp Leu Glu Val Val Thr Ser Thr Trp
545                 550                 555                 560

Val Leu Val Gly Gly Val Leu Ala Ala Leu Ala Ala Tyr Cys Leu Ser
                565                 570                 575

Thr Gly Cys Val Val Ile Val Gly Arg Val Val Leu Ser Gly Lys Pro
            580                 585                 590

Ala Ile Ile Pro Asp Arg Glu Val
            595                 600

<210> SEQ ID NO 19
<211> LENGTH: 159
<212> TYPE: PRT
<213> ORGANISM: Artificial
<220> FEATURE:
<223> OTHER INFORMATION: Synthetic

<400> SEQUENCE: 19

Met Arg Ser Pro Val Phe Thr Asp Asn Ser Ser Pro Pro Val Val Pro
1               5                   10                  15

Gln Ser Phe Gln Val Ala His Leu His Ala Pro Thr Gly Ser Gly Lys
                20                  25                  30

Ser Thr Lys Val Pro Ala Ala Tyr Ala Ala Gln Gly Tyr Lys Val Leu
            35                  40                  45

Val Leu Asn Pro Ser Val Ala Ala Thr Leu Gly Phe Gly Ala Tyr Met
        50                  55                  60

Ser Lys Ala His Gly Ile Asp Pro Asn Ile Arg Thr Gly Val Arg Thr
65                  70                  75                  80

Ile Thr Thr Gly Ser Pro Ile Thr Tyr Ser Thr Tyr Gly Lys Phe Leu

-continued

```
                       85                   90                   95
Ala Asp Gly Gly Cys Ser Gly Gly Ala Tyr Asp Ile Ile Ile Cys Asp
                100                 105                 110

Glu Cys His Ser Thr Asp Ala Thr Ser Ile Leu Gly Ile Gly Thr Val
            115                 120                 125

Leu Asp Gln Ala Glu Thr Ala Gly Ala Arg Leu Val Val Leu Ala Thr
        130                 135                 140

Ala Thr Pro Pro Gly Ser Val Thr Asn Ala Gly Phe Tyr Gly Ile
145                 150                 155
```